United States Patent
Odysseos et al.

(10) Patent No.: US 11,400,160 B2
(45) Date of Patent: Aug. 2, 2022

(54) MULTIFUNCTIONAL CONJUGATES

(71) Applicant: E.P.O.S IASIS Research and Development Limited, Nicosia (CY)

(72) Inventors: Andreani Odysseos, Nicosia (CY); Andreas Evdokiou, South Australia (AU); Anastasios Keramidas, Nicosia (CY)

(73) Assignee: E.P.O.S IASIS Research and Development Limited, Nicosia (CY)

( * ) Notice: Subject to any disclaimer, the term of this patent is extended or adjusted under 35 U.S.C. 154(b) by 56 days.

(21) Appl. No.: 16/628,408

(22) PCT Filed: Jul. 5, 2017

(86) PCT No.: PCT/CY2017/000002
§ 371 (c)(1),
(2) Date: Jan. 3, 2020

(87) PCT Pub. No.: WO2019/007447
PCT Pub. Date: Jan. 10, 2019

(65) Prior Publication Data
US 2020/0164076 A1    May 28, 2020

(51) Int. Cl.
A61K 47/54 (2017.01)
A61P 35/00 (2006.01)
C07F 9/40 (2006.01)

(52) U.S. Cl.
CPC ............ *A61K 47/548* (2017.08); *A61P 35/00* (2018.01); *C07F 9/4006* (2013.01)

(58) Field of Classification Search
None
See application file for complete search history.

(56) References Cited

U.S. PATENT DOCUMENTS

2009/0227544 A1    9/2009    Karpeisky et al.
2014/0356423 A1    12/2014    Angres

FOREIGN PATENT DOCUMENTS

WO    WO-2005-027921    3/2005

OTHER PUBLICATIONS

International Search Report and Written Opinion for International Application No. PCT/CY2017/000002 dated Mar. 28, 2018.
Yamaguchi et al., "Combination of alendronate and genistein synergistically suppresses osteoclastic differentiation of RAW267.4 cells in vitro," Experimental and Therapeutic Medicine, 14(2):1769-1774 (2017).

*Primary Examiner* — Joseph R Kosack
(74) *Attorney, Agent, or Firm* — Foley Hoag LLP; David P. Halstead; Ila S. Anand

(57) ABSTRACT

The present invention provides compounds suitable for use in the treatment of conditions where it is beneficial to halt bone loss and kill cancer cells, particularly in metastases to and primary tumours in the bone and surrounding tissues. Consequently the present invention provides compounds comprising a bisphosphonate moiety linked to a phytochemical, pharmaceutical compositions thereof and methods of treatment of bone diseases and/or proliferative disorders.

21 Claims, 16 Drawing Sheets

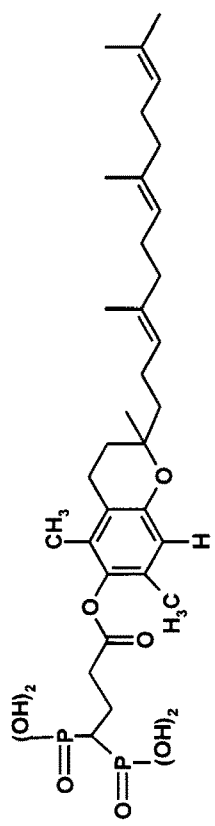
γ-tocotrienol-bpp(OH)
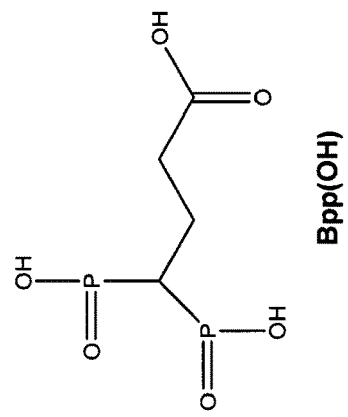
Bpp(OH)
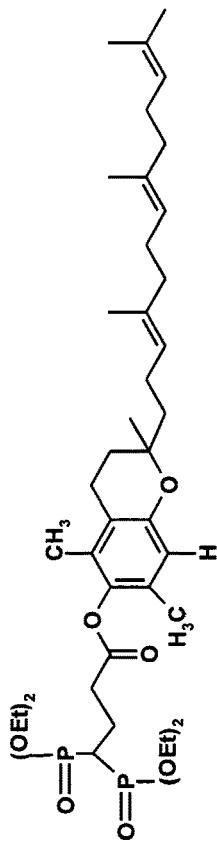
γ-tocotrienol-bpp(OEt)
FIG. 11 (cont.)
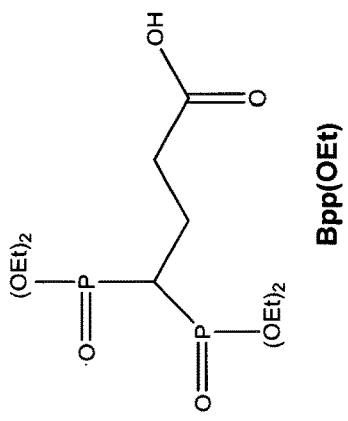
Bpp(OEt)

MULTIFUNCTIONAL CONJUGATES

RELATED APPLICATIONS

This application is a U.S. National Stage application of International No. PCT/CY2017/000002, filed Jul. 5, 2017, which is explicitly incorporated by reference in its entirety.

INTRODUCTION

The present invention provides compounds suitable for use in the treatment of conditions where it is beneficial to halt bone loss and kill cancer cells, particularly metastases to the bone and surrounding tissues. Consequently the present invention provides compounds and pharmaceutical compositions and combinations as' described herein and their use in/methods of treatment of bone diseases and/or proliferative disorders.

BACKGROUND OF THE INVENTION

Metastatic bone disease is very common in patients with solid tumours and is associated with significant pre-terminal debilitation arising from extensive bony destruction, bone pain, pathological fractures, hypercalcaemia and spinal cord compression (Mundy, G. R., *Metastatic bone disease. In: Bone Remodelling and its disorders*. 2 ed.; Martin Dunitz Ltd.: London, 1999; 123-146.

Different forms of bone lesions tend to predominate with certain types of advanced cancer and these vary according to the nature of the primary cancer. For example, multiple myeloma is associated with purely osteolytic lesions, whereas bone lesions in prostate cancer patients are predominantly osteoblastic but may also appear as osteolytic (a. Shimazaki, J. et. al., (1999) *Ad. Exp. Med. Biol.*, 324, 269. b. Berruti, A. et. al., (2000) *J. Urol.* 164, 1248).

In contrast, metastatic bone lesions in patients with breast cancer or primary osteosarcoma can be osteolytic, osteoblastic or mixed, and multiple forms of bone lesions may be present in the same patient (a. Coleman, R. E. et. al., (1987). *Br. J. Cancer* 55, 61; b. Dorfman, H. D., *Osteosarcoma. In: Bone tumours*. ed.; Morsby, Inc.: St. Louis, 1998; 128-252).

In normal bone turnover, the osteolytic activity of osteoclasts is coupled with, and in balance with, the bone forming activity of osteoblasts. For bone cancer, a "vicious cycle" between osteoclasts, bone stromal cells/osteoblasts, and cancer cells exists and is responsible for the progression of bone tumours (Mundy, G. R., *Metastatic bone disease. In: Bone Remodelling and its disorders*. 2 Ed.; Martin Dunitz Ltd.: London, 1999).

Tumour cells associated with osteolytic lesions secrete factors, which stimulate osteoclasts to resorb bone, thereby releasing growth factors from the bone matrix that in turn stimulate the growth of adjacent tumour cells.

In contrast, tumour cells associated with osteoblastic lesions stimulate osteogenesis (Goltzman, D. et. al., (2000) *Cancer* 88, 2903). Osteoblastic lesions are normally associated with a strong osteolytic component and osteogenesis must be preceded by local osteolysis, resulting in decreased bone integrity at the site of tumour growth (Lipton, A. et. al., (2001) *Cancer Invest.*, 20, 45).

Therefore, suppression of bone resorption by targeting osteoclastic activity is an effective approach to inhibit local cancer growth (Saad, F. et. al., (2002) *J. Natl. Cancer Inst.*, 94, 1458).

The anti-resorptive bisphosphonate compounds, such as pamidronate, have been the standard of care for patients with osteolytic lesions from breast cancer and multiple myeloma. The nitrogen-containing bisphosphonate, zoledronic acid, was shown to be effective also in patients with osteoblastic lesions and has proven efficacy in patients with bone lesions arising from a wide variety of solid tumours, including prostate and lung (Kieczykowski, G R.; Jobson, R B.; Melillo, D G. et. al., (1995) *J. Org. Chem.*, 60, 8310; Saad F and Lipton A. *Semin Oncol* 2007; 34(Suppl 4):S17-23)

Although bisphosphonates are highly effective for palliative treatment of skeletal related events associated with bone metastases, in real terms, there have been only minimal improvements in the survival of patients with bone lesions arising from metastatic or primary bone cancer (Kieczykowski, G. R., Jobson, R. B., Melillo, et. al. (1995).*J. Org. Chem.*, 60, 8310)

It is urgently required to develop drugs that selectively target tumour cells within the bone microenvironment and/or exert direct effects on osteoclastic bone resorption.

It is the object of the present invention to provide new compounds which are capable of achieving one or more effects selected from: bone targeting capability, antiproliferative effects in tumour cells; anti-resorptive effects in bone.

Suitably, the present invention provides compounds with bone targeting capability, antiproliferative effects in tumour cells and anti-resorptive effects in bone.

SUMMARY OF THE INVENTION

In a first aspect, the present invention relates to a compound of formula Q-T-L as defined herein.

In a second aspect, the present invention relates to a compound of formula (I) as defined herein.

In a third aspect, the present invention relates to a pharmaceutical composition comprising a compound as defined herein.

In a fourth aspect, the present invention relates to a compound as defined herein, or a pharmaceutically acceptable salt or solvate thereof, for use in therapy.

In a fifth aspect, the present invention relates to a compound as defined herein, or a pharmaceutically acceptable salt or solvate thereof, for use in the treatment of a proliferative disorder.

In a sixth aspect, the present invention relates to a method of treating a proliferative disorder in a patient in need of such treatment, said method comprising administering to said patient a therapeutically effective amount of a compound as defined herein, or a pharmaceutically acceptable salt or solvate thereof.

In a seventh aspect, the present invention relates to a combination comprising a compound, or a pharmaceutically acceptable salt or solvate thereof, as defined herein with one or more additional therapeutic agents.

DETAILED DESCRIPTION OF THE INVENTION

Definitions

Figure 1:
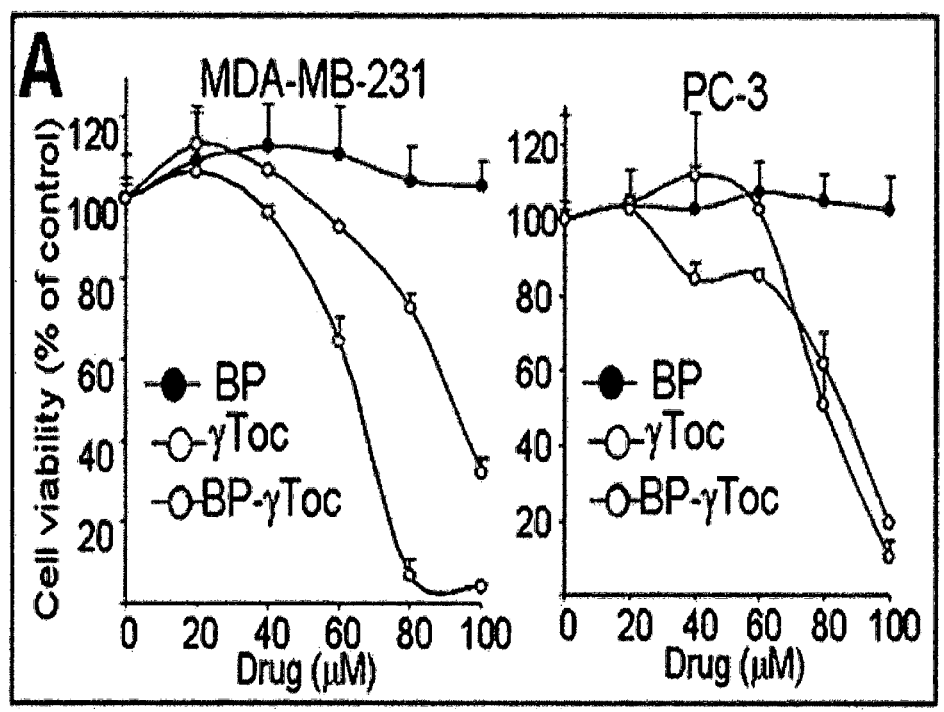
FIG. 1 shows the dose response of the identified compounds in respect of the cell viability of breast and prostate cancer cells.

The compounds and intermediates described herein may be named according to either the IUPAC (International Union for Pure and Applied Chemistry) or CAS (Chemical Abstracts Service) nomenclature systems. It should be understood that unless expressly stated to the contrary, the terms "compounds of Formula I", "compounds of Formula Ia", "compounds of Formula Ib" and the more general term "compounds" refer to and include any and all compounds described by and/or with reference to Formula I, Ia and Ib respectively. It should also be understood that these terms encompasses all stereoisomers, i.e. cis and trans isomers, as well as optical isomers, i.e. R and S enantiomers, of such compounds and all salts thereof, in substantially pure form and/or any mixtures of the foregoing in any ratio. This understanding extends to pharmaceutical compositions and methods of treatment that employ or comprise one or more compounds of the Formula I, Ia and Ib, either by themselves or in combination with additional agents.

The various hydrocarbon-containing moieties provided herein may be described using a prefix designating the minimum and maximum number of carbon atoms in the moiety, e.g. "($C_a$-$C_b$)". For example, ($C_a$-$C_b$)alkyl indicates an alkyl moiety having the integer "a" to the integer "b" number of carbon atoms, inclusive. Certain moieties may also be described according to the minimum and maximum number of members with or without specific reference to a particular atom or overall structure. For example, the terms "a to b membered ring" or "having between a to b members" refer to a moiety having the integer "a" to the integer "b" number of atoms, inclusive.

"About" when used herein in conjunction with a measurable value such as, for example, an amount or a period of time and the like, is meant to encompass reasonable variations of the value, for instance, to allow for experimental error in the measurement of said value.

As used herein "phytochemical" refers to any substance, compound, or chemical that occurs naturally in plants (i.e., organisms belonging to the kingdom Plantae).

As used herein the term "vitamin E derivatives" refers to all optical isomers and racemates of the tocopherols and tocotrienols which occur in human, animal or plant cells, and precursors and metabolites thereof. In a particular embodiment, the term "vitamin E derivative" refers to all optical isomers of the eight natural compounds described as tocopherols or tocotrienols, i.e. α, β-, γ-, and δ-tocopherol and α, β-, γ-, and δ-tocotrienol.

As used herein the term "bisphosphonates" refer to a class of compounds capable of preventing demineralization of bone. Bisphosphonates include zoledronate, alendronate, pamidronate, etidronate, clodronate, tiludronate, neridronate, olpadronate, ibandronate, risedronate.

As used herein by themselves or in conjunction with another term or terms, "alkyl" and "alkyl group" refer to a branched or unbranched saturated hydrocarbon chain. Unless specified otherwise, alkyl groups typically contain 1-10 carbon atoms, such as 1-6 carbon atoms or 1-4 carbon atoms or 1-3 carbon atoms, and can be substituted or unsubstituted. Representative examples include, but are not limited to, methyl, ethyl, n-propyl, i-propyl, n-butyl, i-butyl, s-butyl, t-butyl, n-pentyl, n-hexyl, n-heptyl, n-octyl, n-nonyl, n-decyl, isopropyl, tert-butyl, isobutyl, etc.

As used herein by themselves or in conjunction with another term or terms, "alkylene" and "alkylene group" refer to a branched or unbranched saturated hydrocarbon chain. Unless specified otherwise, alkylene groups typically contain 1-10 carbon atoms, such as 1-6 carbon atoms or 1-3 carbon atoms, and can be substituted or unsubstituted. Representative examples include, but are not limited to, methylene (—$CH_2$—), the ethylene isomers (—CH($CH_3$)— and —$CH_2CH_2$—), the propylene isomers (—CH($CH_3$)$CH_2$—, —CH($CH_2CH_3$)—, —C($CH_3$)$_3$—, and —$CH_2CH_2CH_2$—), etc.

As used herein by themselves or in conjunction with another term or terms, "haloalkyl" and "haloalkyl group" refer to alkyl groups in which one or more hydrogen atoms are replaced by halogen atoms. Haloalkyl includes both saturated alkyl groups as well as unsaturated alkenyl and alkynyl groups. Representative examples include, but are not limited to, —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —CI=$CH_2$, —C≡C—$CF_3$, —$CHFCH_2CH_3$ and —$CHFCH_2CF_3$. Haloalkyl groups can be substituted or unsubstituted. Suitably, a haloalkyl group is selected from $CHF_2$ and $CF_3$, suitably $CF_3$.

As used herein by themselves or in conjunction with another term or terms, "haloalkoxy" and "haloalkoxy group" refer to alkoxy groups (i.e. O-alkyl groups) in which one or more hydrogen atoms are replaced by halogen atoms. Haloalkoxy includes both saturated alkoxy groups as well as unsaturated alkenyl and alkynyl groups. Representative examples include, but are not limited to, —$OCF_3$, —$OCHF_2$, —$OCH_2F$, —$OCF_2CF_3$, —$OCHFCF_3$, —$OCH_2CF_3$, —$OCF_2CH_3$, —$OCHFCH_3$, —$OCF_2CF_2CF_3$, —$OCF_2CH_2CH_3$, —OCF=$CF_2$, —OCCl=$CH_2$, —OCBr=$CH_2$, —$OCHFCH_2CH_3$ and —$OCHFCH_2CF_3$. Haloalkoxy groups can be substituted or unsubstituted.

Suitably, a haloalkyoxy group is selected from —OCHF$_2$ and —OCF$_3$, suitably —OCF$_3$.

As used herein by themselves or in conjunction with another term or terms, "halo" and "halogen" include fluorine, chlorine, bromine and iodine atoms and substituents.

As used herein by themselves or in conjunction with another term or terms, "heteroaryl" and "heteroaryl group" refer to (a) 5 and 6 membered monocyclic aromatic rings, which contain, in addition to carbon atom(s), at least one heteroatom, such as nitrogen, oxygen or sulfur, and (b) 7 to 15 membered bicyclic and tricyclic rings, which contain, in addition to carbon atom(s), at least one heteroatom, such as nitrogen, oxygen or sulfur, and in which at least one of the rings is aromatic. In some instances, a heteroaryl group can contain two or more heteroatoms, which may be the same or different. Heteroaryl groups can be substituted or unsubstituted, and may be bridged, spiro, and/or fused. In some instances, a heteroaryl group may contain 5, 6, or 8 to 15 ring atoms. In other instances, a heteroaryl group may contain 5 to 10 ring atoms, such as 5, 6, 9, or 10 ring atoms. Representative examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.0$^{2,7}$]dodeca-2(7),3,5-trienyl, 12-oxa-10-aza-tricyclo[6.3.1.0$^{2,7}$]dodeca-2(7),3,5-trienyl, 12-aza-tricyclo[7.2.1.0$^{2,7}$]dodeca-2(7),3,5-trienyl, 10-aza-tricyclo[6.3.2.0$^{2,7}$]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. Suitably, a heteroaryl is a 5- or 6-membered heteroaryl ring comprising one, two or three heteroatoms selected from N, O or S.

As used herein by themselves or in conjunction with another term or terms, "aryl" and "aryl group" refer to phenyl and 7-15 membered bicyclic or tricyclic hydrocarbon ring systems, including bridged, spiro, and/or fused ring systems, in which at least one of the rings is aromatic. Aryl groups can be substituted or unsubstituted. Unless specified otherwise, an aryl group may contain 6 ring atoms (i.e., phenyl) or a ring system containing 9 to 15 atoms, such as 9 to 11 ring atoms, or 9 or 10 ring atoms. Representative examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. Suitably an aryl group is phenyl and naphthyl, suitably phenyl.

As used herein by itself or in conjunction with another term or terms, "pharmaceutically acceptable" refers to materials that are generally chemically and/or physically compatible with other ingredients (such as, for example, with reference to a formulation), and/or is generally physiologically compatible with the recipient (such as, for example, a subject) thereof.

As used herein by itself or in conjunction with another term or terms, "pharmaceutical composition" refers to a composition that can be used to treat a disease, condition, or disorder in a subject, including a human.

As used herein by themselves or in conjunction with another term or terms, "stable" and "chemically stable" refer to a compound that is sufficiently robust to be isolated from a reaction mixture with a useful degree of purity. The present application is directed solely to the preparation of stable compounds. When lists of alternative substituents include members which, owing to valency requirements, chemical stability, or other reasons, cannot be used to substitute a particular group, the list is intended to be read in context to include those members of the list that are suitable for substituting the particular group. For example, when considering the degree of optional substitution of a particular moiety, it should be understood that the number of substituents does not exceed the valency appropriate for that moiety.

As used herein by themselves or in conjunction with another term or terms, "subject(s)" and "patient(s)", refer to mammals, including humans.

As used herein by itself or in conjunction with another term or terms, "substituted" indicates that a hydrogen atom on a molecule has been replaced with a different atom or group of atoms and the atom or group of atoms replacing the hydrogen atom is a "substituent." It should be understood that the terms "substituent", "substituents", "moiety", "moieties", "group", or "groups" refer to substituent(s).

As used herein by themselves or in conjunction with another term or terms, "therapeutic" and "therapeutically effective amount" refer to an amount a compound, composition or medicament that (a) inhibits or causes an improvement in a particular disease, condition or disorder; (b) attenuates, ameliorates or eliminates one or more symptoms of a particular disease, condition or disorder; (c) or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c). It should be understood that in, for example, a human or other mammal, a therapeutically effective amount can be determined experimentally in a laboratory or clinical setting, or a therapeutically effective amount may be the amount required by the guidelines of the United States Food and Drug Administration (FDA) or equivalent foreign regulatory body, for the particular disease and subject being treated. It should be appreciated that determination of proper dosage forms, dosage amounts, and routes of administration is within the level of ordinary skill in the pharmaceutical and medical arts.

As used herein whether by themselves or in conjunction with another term or terms, "treating", "treated" and "treatment", refer to and include prophylactic, ameliorative, palliative, and curative uses and results. In some embodiments, the terms "treating", "treated", and "treatment" refer to curative uses and results as well as uses and results that diminish or reduce the severity of a particular condition, characteristic, symptom, disorder, or disease described herein. For example, treatment can include diminishment of several symptoms of a condition or disorder or complete eradication of said condition or disorder. It should be understood that the term "prophylactic" as used herein is not absolute but rather refers to uses and results where the administration of a compound or composition diminishes the likelihood or seriousness of a condition, symptom, or disease state, and/or delays the onset of a condition, symptom, or disease state for a period of time.

As used herein, a "therapeutic agent", whether used alone or in conjunction with another term or terms, refers to any compound, i.e. a drug, that has been found to be useful in the treatment of a disease, disorder or condition and is not described by Formula I. It should be understood that a therapeutic agent may not be approved by the FDA or an equivalent foreign regulatory body.

A "therapeutically effective amount" means the amount of a compound that, when administered to a subject or patient for treating a disease, is sufficient to effect such treatment for the disease. The "therapeutically effective amount" will vary depending on the compound, the disease and its severity and the age, weight, etc., of the subject or patient to be treated.

Compounds
Phytochemical

In one aspect, the present invention relates to a compound of formula Q-T-L wherein Q is a bisphosphonate moiety, T is linker and L is an anti-osteolytic or osteoinductive phytochemical.

In one embodiment, L is an anti-osteolytic and osteoinductive phytochemical.

In another embodiment, the anti-osteolytic and/or osteoinductive phytochemical is a phenolic phytochemical, suitably selected from a phenolic flavonoid, a poly(oxo)phenol, a phenolic terpene and a phenolic vitamin E derivative.

In one embodiment, the anti-osteolytic and/or osteoinductive phytochemical is a selected from the group consisting of vitamin E derivatives, reserveratrols, retinols, flavonoids, terpenes, germacrane sesquiterpenes, matairesinol, xanthine derivatives, hallucinogens, isoflavones, lignans, flavones, flavanols, flavanones, catechins, epigallocatechin gallate (EGCG), stilbenes, cannabinoids, curcuminoids, caryophyllene type sesquiterpene lactone, zerumbone, andrographolide, natural diterpenoid lactone, carotenoids, quercetin, lycopene, phenolics, resveratrol, phloridzin, pectin (suitably derived from tomato, grapes, apples, and citrus fruits), vitamin D, genistein, curcumin (suitably from turmeric), capsaicin, (red pepper), eugenol, (suitably from cloves), gingerol, (suitably from ginger), anethol (suitably from cumin, anise, or fennel), ursolic acid (basil and rosemary), diallyl sulfide, S-allylmercaptocysteine, ajoene (suitably from garlic), ellagic acid (suitably from pomegranate), daidzein, medicarpin (suitably from legumes) and equol.

In one embodiment, the anti-osteolytic and/or osteoinductive phytochemical is a selected from the group consisting of vitamin E derivatives, reserveratrols, retinols, flavonoids, terpenes, germacrane sesquiterpenes, isoflavones, lignans, flavones, Flavanols, flavanones, catechins, stilbenes, cannabinoids, curcuminoids, caryophyllene type sesquiterpene lactone, carotenoids, quercetin and phenolics.

In one embodiment, the anti-osteolytic and/or osteoinductive phytochemical is a selected from the group consisting of α-, β-, γ-, or δ-tocopherol, α-, β-, γ- or δ-tocotrienol, eupafolin, carnosol, scutellarein, genkwanin, kaempferol, acacetin, rosmarinic acid, rosmanol, cirsimaritin, luteolin and 7-epi-rosmanol matairesinol, epigallocatechin gallate (EGCG), zerumbone, andrographolide, quercetin, lycopene, resveratrol, phloridzin, vitamin D, genistein, curcumin (suitably from turmeric), capsaicin, (red pepper), eugenol, (suitably from cloves), gingerol, (suitably from ginger), anethol (suitably from cumin, anise, or fennel), ursolic acid (basil and rosemary), diallyl sulfide, S-allylmercaptocysteine, ajoene (suitably from garlic), ellagic acid (suitably from pomegranate), daidzein, medicarpin (suitably from legumes) and equol.

In another embodiment, the anti-osteolytic and/or osteoinductive phytochemical is a vitamin E derivative.

In one embodiment, the anti-osteolytic and/or osteoinductive phytochemical is selected from α-, β-, γ-, or δ-tocopherol, α-, β-, γ- or δ-tocotrienol, eupafolin, carnosol, scutellarein, genkwanin, kaempferol, acacetin, rosmarinic acid, rosmanol, cirsimaritin, luteolin and 7-epi-rosmanol.

In one embodiment, the anti-osteolytic and/or osteoinductive phytochemical is selected from α-, β-, γ-, or δ-tocopherol and α-, β-, γ- or δ-tocotrienol.

Bisphosphonate

In one embodiment, the bisphosphonate is selected from zoledronate, alendronate, pamidronate, etidronate, clodronate, tiludronate, neridronate, olpadronate, ibandronate, risedronate.

In another embodiment, the bisphosphonate moiety is a moiety according to general formula (IIa) or (IIb):

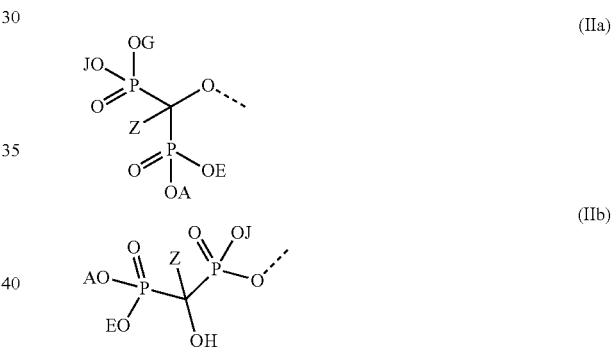

wherein,

A, E, J and G are independently selected from hydrogen and $C_{1-6}$ alkyl;

Z is selected from hydrogen, halogen, hydroxyl, aryl, heteroaryl, and $C_{1-6}$ alkyl, wherein said aryl, heteroaryl and $C_{1-6}$ alkyl may optionally be substituted by one or more $R^z$ groups;

$R^z$ is selected from hydrogen, hydroxyl, halogen, COOH, CN, $C_{1-6}$ haloalkyl, $C_{1-6}$ haloalkoxy, $C_{3-6}$ cycloalkyl, $C_{1-6}$ alkyl and O—$C_{1-6}$ alkyl; and the dotted line indicates a bond to linker T.

Linker

In one embodiment, linker T is an optionally substituted alkylene group.

In another embodiment, linker T, may be a direct bond.

In another embodiment, linker T together with a phenolic oxygen moiety of the phytochemical, L, may be an ester, suitably a $C_1$-$C_3$ alkyl ester.

In another embodiment, linker T together with a phenolic oxygen moiety of the phytochemical, L, may be an ether, suitably a $C_1$-$C_3$ alkyl ether.

In another aspect, the present invention relates to a compound of formula (I), or a salt or solvate thereof:

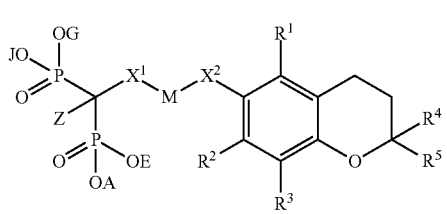

(I)

wherein,
A, E, J and G are independently selected from hydrogen and $C_{1-6}$ alkyl;
Z is selected from hydrogen, halogen, hydroxyl, aryl, heteroaryl, and $C_{1-6}$ alkyl, wherein said aryl, heteroaryl and $C_{1-6}$ alkyl may optionally be substituted by one or more $R^z$ groups;
$R^z$ is selected from hydrogen, hydroxyl, halogen, COOH, CN, $C_{1-6}$ haloalkyl, $C_{1-6}$ haloalkoxy, $C_{3-6}$ cycloalkyl, $C_{1-6}$ alkyl and O—$C_{1-6}$ alkyl;
$X^1$ is a $(CR'R'')_n$ group and $X^2$ is a $(CR'R'')_m$ group, wherein R' and R" are independently selected from hydrogen and $C_{1-6}$ alkyl and m and n are numbers independently selected from 0 to 5;
M is selected from N(R), S, O and C(O)O; wherein R is selected from hydrogen and $C_{1-6}$ alkyl;
$R^1$, $R^2$ and $R^3$ are independently selected from hydrogen and $C_{1-6}$ alkyl;
$R^4$ is a $C_{1-6}$ alkyl group;
$R^5$ is selected from:

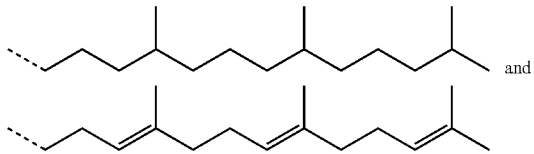

and

Particular embodiments of the compounds of the formula I, or salts and/or solvates thereof, (and, where applicable, formula (IIa) and (IIb)) wherein alternative definitions of each of A, E, J, G, Z, $X^1$, $X^2$, R', R", m and n, R, $R^1$, $R^2$, $R^3$, $R^4$, and $R^5$ are defined in the following numbered paragraphs. Where not described otherwise, substituents have the same meaning as described for formula (I) above.
(1) A, E, J and G are independently selected from hydrogen, methyl and ethyl.
(2) A, E, J and G are all the same and selected from hydrogen, methyl and ethyl.
(3) A, E, J and G are all the same and selected from hydrogen and ethyl.
(4) Z is selected from hydrogen, halogen, hydroxyl and $C_{1-6}$ alkyl;
(5) Z is selected from hydrogen, hydroxyl, methyl, ethyl and chloro.
(6) Z is selected from hydrogen, hydroxyl and methyl.
(7) Z is hydrogen.
(8) R' and R" are independently selected from hydrogen and methyl.
(9) $X^1$ is $(CH_2)_n$.
(10) $X^2$ is $(CH_2)_m$.
(11) n is 1 to 5.
(12) n is 2 to 5
(13) n is 2 to 4
(14) n is 2 to 3
(15) m is 1 to 5
(16) m is 0
(17) M is selected from NR, O and C(O)O.
(18) M is selected from O and C(O)O.
(19) M is selected from S, O and C(O).
(20) R is selected from hydrogen and methyl.
(21) $R^1$, $R^2$ and $R^3$ are independently selected from hydrogen, methyl and ethyl.
(22) $R^1$, $R^2$ and $R^3$ are independently selected from hydrogen and methyl.
(23) $R^1$, $R^2$ and $R^3$ are all methyl.
(24) $R^1$ is methyl, $R^2$ is hydrogen and $R^3$ is methyl.
(25) $R^1$ is hydrogen, $R^2$ is methyl and $R^3$ is methyl.
(26) $R^1$ is hydrogen, $R^2$ is hydrogen and $R^3$ is methyl.
(27) $R^4$ is methyl.
(28) $R^5$ is
(29) $R^5$ is

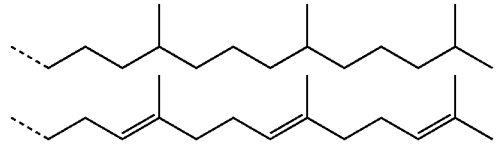

In one embodiment, M is O, m is O, $X^1$ is $CH_2$ and n has any one of the definitions in paragraphs (10) to (13).
In one embodiment, M is C(O)O, $X^1$ is $CH_2$ and n has any one of the definitions in paragraphs (10) to (13).
In one embodiment, M is N(R), m is 0, $X^1$ is $CH_2$ and n has any one of the definitions in paragraphs (10) to (13).
In one embodiment, M is N(Me), $X^1$ and $X^2$ are $CH_2$, m is 5 and n has any one of the definitions in paragraphs (10) to (13).
In one embodiment, M is N(Me), $X^1$ and $X^2$ are $CH_2$, and n is 2.
In one embodiment, Z is H, M is O, m is O, $X^1$ is $CH_2$ and n has any one of the definitions in paragraphs (10) to (13).
In one embodiment, Z is H, M is C(O)O, $X^1$ is $CH_2$ and n has any one of the definitions in paragraphs (10) to (13).
In one embodiment, Z is OH, M is N(R), m is 0, $X^1$ is $CH_2$ and n has any one of the definitions in paragraphs (10) to (13).
In one embodiment, Z is OH, M is N(Me), $X^1$ and $X^2$ are $CH_2$, m is 5 and n has any one of the definitions in paragraphs (10) to (13).
In one embodiment, Z is OH, M is N(Me), $X^1$ and $X^2$ are $CH_2$, and n is 2.
In one embodiment, M is N(R), m is 0, $X^1$ is $CH_2$ and n has any one of the definitions in paragraphs (10) to (13).
In one embodiment, M is O, m is 0, $X^1$ is $CH_2$ and n has any one of the definitions in paragraphs (10) to (13) and $R^1$, $R^2$ and $R^3$ are independently selected from hydrogen and methyl.
In one embodiment, M is C(O)O, $X^1$ is $CH_2$ and n has any one of the definitions in paragraphs (10) to (13), and $R^1$, $R^2$ and $R^3$ are independently selected from hydrogen and methyl.
In one embodiment, M is N(R), m is 0, $X^1$ is $CH_2$ and n has any one of the definitions in paragraphs (10) to (13), and $R^1$, $R^2$ and $R^3$ are independently selected from hydrogen and methyl.

In one embodiment, M is N(Me), $X^1$ and $X^2$ are $CH_2$, m is 5 and n has any one of the definitions in paragraphs (10) to (13), and $R^1$, $R^2$ and $R^3$ are independently selected from hydrogen and methyl.

In one embodiment, M is N(Me), $X^1$ and $X^2$ are $CH_2$, and n is 2, and $R^1$, $R^2$ and $R^3$ are independently selected from hydrogen and methyl.

In one embodiment, M is O, m is 0, $X^1$ is $CH_2$ and n has any one of the definitions in paragraphs (10) to (13) and $R^4$ is methyl.

In one embodiment, M is C(O)O, $X^1$ is $CH_2$ and n has any one of the definitions in paragraphs (10) to (13) and $R^4$ is methyl.

In one embodiment, M is N(R), m is 0, $X^1$ is $CH_2$ and n has any one of the definitions in paragraphs (10) to (13) and $R^4$ is methyl.

In one embodiment, M is N(Me), $X^1$ and $X^2$ are $CH_2$, m is 5 and n has any one of the definitions in paragraphs (10) to (13) and $R^4$ is methyl.

In one embodiment, M is N(Me), $X^1$ and $X^2$ are $CH_2$, and n is 2, and $R^4$ is methyl.

In one embodiment, Z is H, M is O, m is O, $X^1$ is $CH_2$ and n has any one of the definitions in paragraphs (10) to (13), and $R^4$ is methyl.

In one embodiment, Z is H, M is C(O)O, $X^1$ is $CH_2$ and n has any one of the definitions in paragraphs (10) to (13), and $R^4$ is methyl.

In one embodiment, Z is OH, M is N(R), m is 0, $X^1$ is $CH_2$ and n has any one of the definitions in paragraphs (10) to (13), and $R^4$ is methyl.

In one embodiment, Z is OH, M is N(Me), $X^1$ and $X^2$ are $CH_2$, m is 5 and n has any one of the definitions in paragraphs (10) to (13), and $R^4$ is methyl.

In one embodiment, Z is OH, M is N(Me), $X^1$ and $X^2$ are $CH_2$, and n is 2, and $R^4$ is methyl.

In one embodiment, M is N(R), m is 0, $X^1$ is $CH_2$ and n has any one of the definitions in paragraphs (10) to (13), and $R^4$ is methyl.

In one embodiment, M is O, m is O, $X^1$ is $CH_2$ and n has any one of the definitions in paragraphs (10) to (13) and $R^1$, $R^2$ and $R^3$ are independently selected from hydrogen and methyl, and $R^4$ is methyl.

In one embodiment, M is C(O)O, $X^1$ is $CH_2$ and n has any one of the definitions in paragraphs (10) to (13), and $R^1$, $R^2$ and $R^3$ are independently selected from hydrogen and methyl, and $R^4$ is methyl.

In one embodiment, M is N(R), m is 0, $X^1$ is $CH_2$ and n has any one of the definitions in paragraphs (10) to (13), and $R^1$, $R^2$ and $R^3$ are independently selected from hydrogen and methyl, and $R^4$ is methyl.

In one embodiment, M is N(Me), $X^1$ and $X^2$ are $CH_2$, m is 5 and n has any one of the definitions in paragraphs (10) to (13), and $R^1$, $R^2$ and $R^3$ are independently selected from hydrogen and methyl, and $R^4$ is methyl.

In one embodiment, M is N(Me), $X^1$ and $X^2$ are $CH_2$, and n is 2, and $R^1$, $R^2$ and $R^3$ are independently selected from hydrogen and methyl, and $R^4$ is methyl.

In one embodiment, A, E, J and G are all ethyl and $R^4$ is methyl.

In one embodiment, A, E, J and G are all ethyl, $R^4$ is methyl and $R^1$, $R^2$ and $R^3$ are independently selected from hydrogen and methyl.

In one embodiment, A, E, J and G are all ethyl, $R^4$ is methyl and $R^1$, $R^2$ and $R^3$ are independently selected from hydrogen and methyl, and M is selected from any one of paragraphs (16) to (18).

In one embodiment, A, E, J and G are all ethyl, $R^4$ is methyl and $R^1$, $R^2$ and $R^3$ are independently selected from hydrogen and methyl, and M is selected from any one of paragraphs (16) to (18) and m is 0.

In one embodiment, A, E, J and G are all hydrogen and $R^4$ is methyl.

In one embodiment, A, E, J and G are all hydrogen, $R^4$ is methyl and $R^1$, $R^2$ and $R^3$ are independently selected from hydrogen and methyl.

In one embodiment, A, E, J and G are all hydrogen, $R^4$ is methyl and $R^1$, $R^2$ and $R^3$ are independently selected from hydrogen and methyl, and M is selected from any one of paragraphs (16) to (18).

In one embodiment, A, E, J and G are all hydrogen, $R^4$ is methyl and $R^1$, $R^2$ and $R^3$ are independently selected from hydrogen and methyl, and M is selected from any one of paragraphs (16) to (18) and m is 0.

In one embodiment, the present invention relates to a compound of formula Ia:

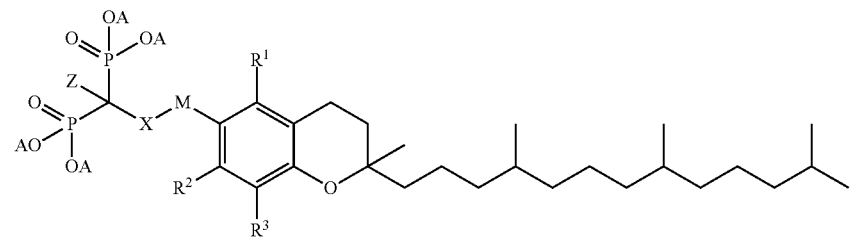

(Ia)

wherein,
A is selected from hydrogen and $C_{1-3}$ alkyl;
Z is selected from hydrogen or hydroxyl;
X is selected from $(CH)_n$ and n is a number between 1 and 5;
M is selected from O and C(O)O; and
$R^1$, $R^2$ and $R^3$ are independently selected from hydrogen and $C_{1-3}$ alkyl.

Particular embodiments of the compounds of the formula (Ia), or salts and/or solvates thereof, wherein alternative definitions of each of A, Z, X, n, $R^1$, $R^2$ and $R^3$ are defined in the following numbered paragraphs. Where not described otherwise, substituents have the same meaning as described for formula (Ia) above.

(1) A is selected from hydrogen, methyl and ethyl
(2) A is hydrogen
(3) A is ethyl
(4) Z is hydrogen
(5) Z is hydroxyl
(6) n is 2 to 5

(7) n is 2 to 4
(8) n is 2 to 3
(9) n is 2
(10) n is 3
(11) M is O
(12) M is C(O)O
(13) $R^1$, $R^2$ and $R^3$ are independently selected from hydrogen, methyl and ethyl.
(14) $R^1$, $R^2$ and $R^3$ are independently selected from hydrogen and methyl.
(15) $R^1$, $R^2$ and $R^3$ are all methyl.
(16) $R^1$ is methyl, $R^2$ is hydrogen and $R^3$ is methyl.
(17) $R^1$ is hydrogen, $R^2$ is methyl and $R^3$ is methyl.
(18) $R^1$ is hydrogen, $R^2$ is hydrogen and $R^3$ is methyl.

In one embodiment, A is hydrogen, Z is OH, M is O and n is selected from any one of the definitions (6) to (10).

In one embodiment, A is ethyl, Z is OH, M is O and n is selected from any one of the definitions (6) to (10).

In one embodiment, A is hydrogen, Z is H, M is C(O)O and n is selected from any one of the definitions (6) to (10).

In one embodiment, A is ethyl, Z is H, M is C(O)O and n is selected from any one of the definitions (6) to (10).

In one embodiment, n is 2 to 3 and $R^1$, $R^2$ and $R^3$ are selected from any of the definitions in paragraphs (13) to (18).

In one embodiment, M is O, Z is OH, n is 2 to 3 and $R^1$, $R^2$ and $R^3$ are selected from any of the definitions in paragraphs (13) to (18).

In one embodiment, M is C(O)O, Z is H, n is 2 to 3 and $R^1$, $R^2$ and $R^3$ are selected from any of the definitions in paragraphs (13) to (18).

In one embodiment, A is hydrogen, M is O, Z is OH, n is 2 to 3 and $R^1$, $R^2$ and $R^3$ are selected from any of the definitions in paragraphs (13) to (18)

In one embodiment, A is hydrogen, M is C(O)O, Z is H, n is 2 to 3 and $R^1$, $R^2$ and $R^3$ are selected from any of the definitions in paragraphs (13) to (18).

In one embodiment, A is ethyl, M is O, Z is OH, n is 2 to 3 and $R^1$, $R^2$ and $R^3$ are selected from any of the definitions in paragraphs (13) to (18)

In one embodiment, A is ethyl, M is C(O)O, Z is H, n is 2 to 3 and $R^1$, $R^2$ and $R^3$ are selected from any of the definitions in paragraphs (13) to (18).

In one embodiment, the present invention relates to a compound of formula Ib:

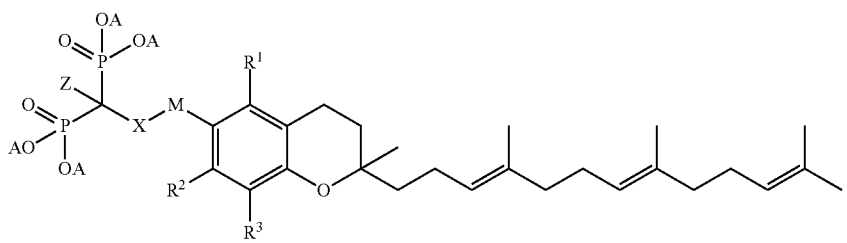

(Ib)

wherein,
A is selected from hydrogen and $C_{1-3}$ alkyl;
Z is selected from hydrogen and hydroxyl;
X is selected from $(CH)_n$ and n is a number between 1 and 5;
M is selected from O and C(O)O; and
$R^1$, $R^2$ and $R^3$ are independently selected from hydrogen and $C_{1-3}$ alkyl.

Particular embodiments of the compounds of the formula (Ib), or salts and/or solvates thereof, wherein alternative definitions of each of A, Z, X, n, $R^1$, $R^2$ and $R^3$ are defined in the following numbered paragraphs. Where not described otherwise, substituents have the same meaning as described for formula (Ib) above.

(19) A is selected from hydrogen, methyl and ethyl
(20) A is hydrogen
(21) A is ethyl
(22) Z is hydrogen
(23) Z is hydroxyl
(24) n is 2 to 5
(25) n is 2 to 4
(26) n is 2 to 3
(27) n is 2
(28) n is 3
(29) M is O
(30) M is C(O)O
(31) $R^1$, $R^2$ and $R^3$ are independently selected from hydrogen, methyl and ethyl.
(32) $R^1$, $R^2$ and $R^3$ are independently selected from hydrogen and methyl.
(33) $R^1$, $R^2$ and $R^3$ are all methyl.
(34) $R^1$ is methyl, $R^2$ is hydrogen and $R^3$ is methyl.
(35) $R^1$ is hydrogen, $R^2$ is methyl and $R^3$ is methyl.
(36) $R^1$ is hydrogen, $R^2$ is hydrogen and $R^3$ is methyl.

In one embodiment, A is hydrogen, Z is OH, M is O and n is selected from any one of the definitions (6) to (10).

In one embodiment, A is ethyl, Z is OH, M is O and n is selected from any one of the definitions (6) to (10).

In one embodiment, A is hydrogen, Z is H, M is C(O)O and n is selected from any one of the definitions (6) to (10).

In one embodiment, A is ethyl, Z is H, M is C(O)O and n is selected from any one of the definitions (6) to (10).

In one embodiment, n is 2 to 3 and $R^1$, $R^2$ and $R^3$ are selected from any of the definitions in paragraphs (13) to (18).

In one embodiment, M is O, Z is OH, n is 2 to 3 and $R^1$, $R^2$ and $R^3$ are selected from any of the definitions in paragraphs (13) to (18).

In one embodiment, M is C(O)O, Z is H, n is 2 to 3 and $R^1$, $R^2$ and $R^3$ are selected from any of the definitions in paragraphs (13) to (18).

In one embodiment, A is hydrogen, M is O, Z is OH, n is 2 to 3 and $R^1$, $R^2$ and $R^3$ are selected from any of the definitions in paragraphs (13) to (18)

In one embodiment, A is hydrogen, M is C(O)O, Z is H, n is 2 to 3 and $R^1$, $R^2$ and $R^3$ are selected from any of the definitions in paragraphs (13) to (18).

In one embodiment, A is ethyl, M is O, Z is OH, n is 2 to 3 and $R^1$, $R^2$ and $R^3$ are selected from any of the definitions in paragraphs (13) to (18)

In one embodiment, A is ethyl, M is C(O)O, Z is H, n is 2 to 3 and $R^1$, $R^2$ and $R^3$ are selected from any of the definitions in paragraphs (13) to (18).

In one embodiment, the compound of formula (I) is selected from one or more of the group consisting of:

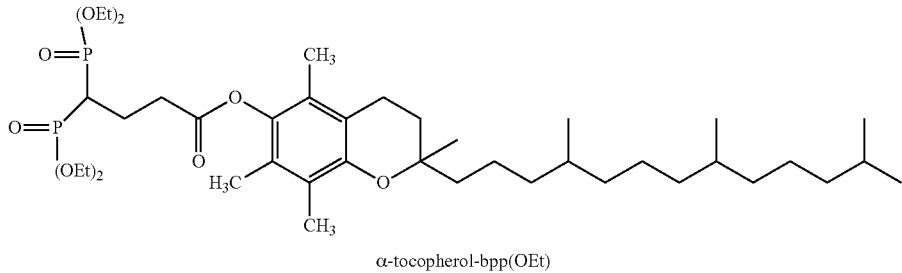

α-tocopherol-bpp(OEt)

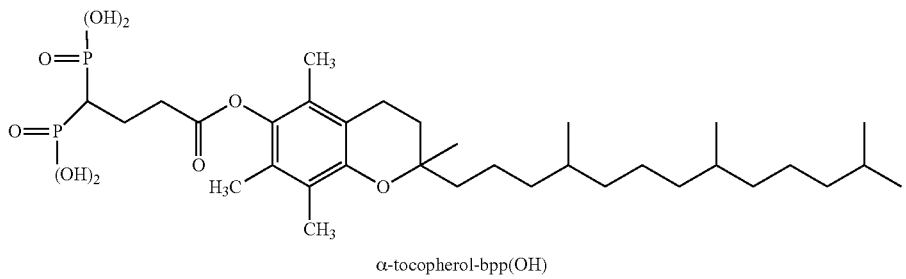

α-tocopherol-bpp(OH)

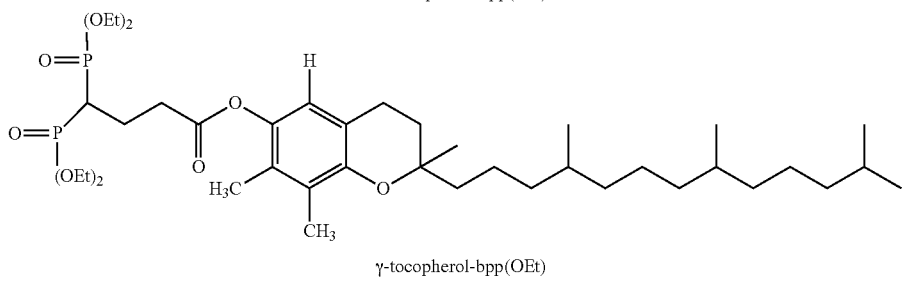

γ-tocopherol-bpp(OEt)

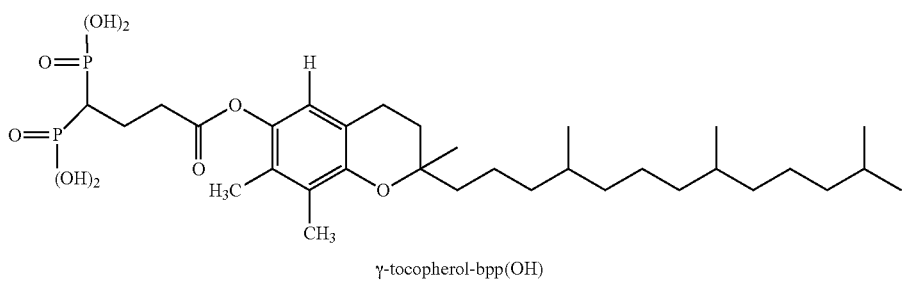

γ-tocopherol-bpp(OH)

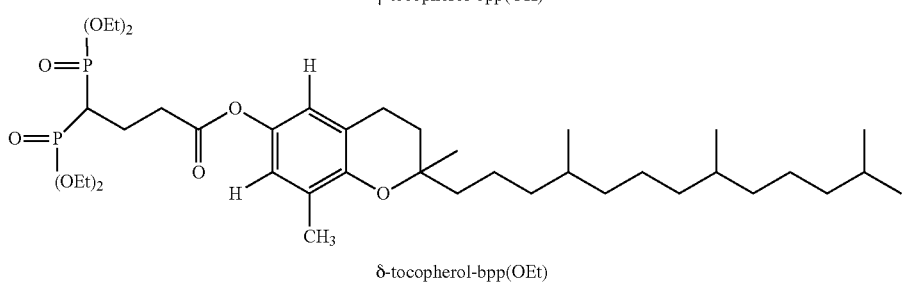

δ-tocopherol-bpp(OEt)

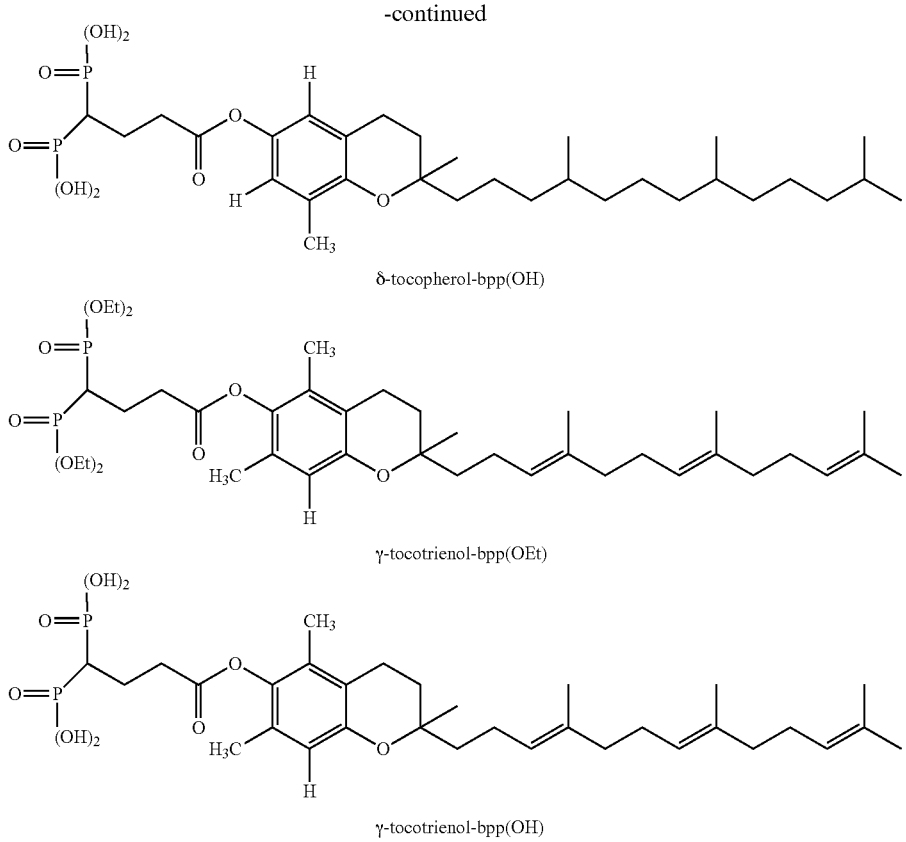

δ-tocopherol-bpp(OH)

γ-tocotrienol-bpp(OEt)

γ-tocotrienol-bpp(OH)

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Salts and Solvates

The compounds (including final products and intermediates) described herein may be isolated and used per se or may be isolated in the form of a salt, suitably pharmaceutically acceptable salts. It should be understood that the terms "salt(s)" and "salt form(s)" used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more.

Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved by the FDA or equivalent foreign regulatory body for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In one embodiment, the compounds of formula are isolated as pharmaceutically acceptable salts.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents) and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Certain compounds of the invention may exist in solvated as well as unsolvated forms such as, for example, hydrated forms. It is to be understood that the invention encompasses all such solvated forms that possess antiproliferative activity.

Polymorphs

It is also to be understood that certain compounds of the invention may exhibit polymorphism, and that the invention encompasses all such forms that possess antiproliferative activity.

Isomers

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

Certain compounds of invention may have one or more asymmetric centers and therefore can exist in a number of stereoisomeric configurations. Consequently, such compounds can be synthesized and/or isolated as mixtures of enantiomers and/or as individual (pure) enantiomers, and, in the case of two or more asymmetric centers, single diastereomers and/or mixtures of diastereomers. It should be understood that the present application includes all such enantiomers and diastereomers and mixtures thereof in all ratios.

Isotopes

The compounds of the present invention are described herein using structural formulas that do not specifically recite the mass numbers or the isotope ratios of the constituent atoms. As such it is intended that the present application includes compounds in which the constituent atoms are present in any ratio of isotope forms. For example, carbon atoms may be present in any ratio of $^{12}C$, $^{13}C$, and $^{14}C$; hydrogen atoms may be present in any ratio of $^{1}H$, $^{2}H$, and $^{3}H$; etc. Preferably, the constituent atoms in the compounds of the present invention are present in their naturally occurring ratios of isotope forms.

Prodrugs and Metabolites

The compounds of invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the invention and in-vivo cleavable amide derivatives that may be formed at a carboxy group or an amino group in a compound of the invention.

Accordingly, the present invention includes those compounds of the invention as defined hereinbefore when made available by organic synthesis and when made available within the human or animal body by way of cleavage of a pro-drug thereof. Accordingly, the present invention includes those compounds of the invention that are produced by organic synthetic means and also such compounds that are produced in the human or animal body by way of metabolism of a precursor compound, that is a compound of the invention may be a synthetically-produced compound or a metabolically-produced compound.

A suitable pharmaceutically acceptable pro-drug of a compound of the invention is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);

b) Design of Pro-drugs, edited by H. Bundgaard, (Elsevier, 1985);

c) A Textbook of Drug Design and Development, edited by Krogsgaard-Larsen and H. Bundgaard, Chapter 5 "Design and Application of Pro-drugs", by H. Bundgaard p. 113-191 (1991);

d) H. Bundgaard, *Advanced Drug Delivery Reviews*, 8, 1-38 (1992);

e) H. Bundgaard, et al., *Journal of Pharmaceutical Sciences*, 77, 285 (1988);

f) N. Kakeya, et al., *Chem. Pharm. Bull.*, 32, 692 (1984);

g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable pro-drug of a compound of the invention that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the f invention that possesses a hydroxy group is, for example, an in vivo cleavable ester or ether thereof. An in vivo cleavable ester or ether of a compound of the invention containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the f invention that possesses a carboxy group is, for example, an in vivo cleavable amide thereof, for example an amide formed with an amine such as ammonia, a $C_{1-4}$alkylamine such as methylamine, a $(C_{1-4}alkyl)_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$ alkylamine such as benzylamine and amino acids such as glycine or an ester thereof.

A suitable pharmaceutically acceptable pro-drug of a compound of the invention that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the invention may be exerted in part by one or more metabolites that are formed within the human or animal body after administration of a compound of the invention. As stated hereinbefore, the in vivo effects of a compound of the invention may also be exerted by way of metabolism of a precursor compound (a pro-drug).

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the invention will naturally vary according to the nature and severity of the conditions, the age and sex of the animal or patient and the route of administration, according to well known principles of medicine.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the person skilled in the art. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides a compound, or a pharmaceutically acceptable salt, hydrate or solvate thereof, or a pharmaceutical composition as defined herein for use in therapy.

The present invention provides a compound, or a pharmaceutically acceptable salt, hydrate or solvate thereof, or a pharmaceutical composition as defined herein for use in the treatment of a proliferative condition.

The present invention provides a compound, or a pharmaceutically acceptable salt, hydrate or solvate thereof, or a pharmaceutical composition as defined herein for use in the treatment of cancer. In a particular embodiment, the cancer is human cancer.

The present invention provides a compound, or a pharmaceutically acceptable salt, hydrate or solvate thereof, or a pharmaceutical composition as defined herein for use in the treatment of bone cancer (including primary bone cancer and bone metastases).

The present invention provides a method of treating a proliferative disorder in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of treating cancer in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of treating bone cancer (including primary bone cancer and bone metastases) in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a use of a compound, or a pharmaceutically acceptable salt, hydrate or solvate thereof, as defined herein in the manufacture of a medicament for the treatment of a proliferative condition.

The present invention provides a use of a compound, or a pharmaceutically acceptable salt, hydrate or solvate thereof, as defined herein in the manufacture of a medicament for the treatment of cancer. Suitably, the medicament is for use in the treatment of human cancers.

The present invention provides a use of a compound, or a pharmaceutically acceptable salt, hydrate or solvate thereof, as defined herein in the manufacture of a medicament for the treatment of bone cancer (including primary bone cancer and bone metastases).

The term "proliferative disorder" as used herein pertains to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell/tissue may be treated, including but not limited to, lung, bone, colon, breast, ovarian, prostate, liver, pancreas, brain, and skin.

The compounds of the invention have particular application in the treatment of metastatic cancers, particularly secondary bone cancers.

The anti-cancer effect may arise through one or more mechanisms, including but not limited to, the regulation of cell proliferation or the promotion of apoptosis (programmed cell death).

In a particular embodiment of the invention, the proliferative condition to be treated is cancer. For example, lung cancer, bone cancer, colon cancer, breast cancer, ovarian cancer, prostate cancer, liver cancer, kidney cancer, thyroid cancer, pancreatic cancer, brain cancer and skin cancer.

In a particular embodiment of the invention, the proliferative disorder is bone cancer. In another embodiment, the proliferative disorder is metastatic breast cancer. In another embodiment, the proliferative disorder is metastatic prostate cancer. In another embodiment, the proliferative disorder is metastatic lung cancer. In another embodiment, the proliferative disorder is metastatic kidney cancer. In another embodiment, the proliferative disorder is metastatic thyroid cancer.

The compounds of the invention have also been found to have anti-resorptive effects on bone. Consequently, the compounds of the invention have particular use in conditions wherein inhibition of bone resorption is of benefit. For instance, the compounds of the invention may be for use in the treatment of Paget's disease of bone and osteoporosis.

The compounds of the invention have also been found to be inhibitors of osteoclastogenesis. Consequently, the compounds of the invention have particular use in conditions wherein inhibition of osteoclastogenesis is beneficial. For instance, the compounds of the invention may be for use in the treatment of Paget's disease of bone and osteoporosis.

The present invention provides a compound, or a pharmaceutically acceptable salt, hydrate or solvate thereof, or a pharmaceutical composition as defined herein for use in the treatment of a disease or condition associated with bone loss.

The present invention provides a method of treating a disease or condition associated with bone loss in a patient in need of such treatment, said method comprising administering to said patient a therapeutically effective amount of a compound, or a pharmaceutically acceptable salt, hydrate or solvate thereof, or a pharmaceutical composition as defined herein The present invention provides a use of a compound, or a pharmaceutically acceptable salt, hydrate or solvate thereof, as defined herein in the manufacture of a medicament for the treatment of a disease or condition associated with bone loss.

In one embodiment, the disease or condition associated with bone loss is selected from Paget's disease of bone, osteoporosis, alveolar bone loss disease, degenerative bone loss disease, dental bone loss disease and bone loss associated with thyroid disease. In another embodiment, the disease or condition associated with bone loss is selected from Paget's disease of bone and osteoporosis.

The compounds of the invention have also been found to have bone anabolic effects. Consequently, the compounds of the invention have particular use in conditions wherein an anabolic effect on bone is beneficial. For instance, the compounds of the invention may be for use in the treatment of Paget's disease of bone and osteoporosis.

The compounds of the invention have also been found to have osteogenesis effects. Consequently, the compounds of the invention have particular use in conditions wherein osteogenesis is beneficial. For instance, the compounds of the invention may be for use in the treatment of Paget's disease of bone and osteoporosis.

The present invention provides a compound, or a pharmaceutically acceptable salt, hydrate or solvate thereof, or a pharmaceutical composition as defined herein for use in the treatment of a disease or condition ameliorated by osteogenesis.

The present invention provides a method of treating a disease or condition ameliorated by osteogenesis in a patient in need of such treatment, said method comprising administering to said patient a therapeutically effective amount of a compound, or a pharmaceutically acceptable salt, hydrate or solvate thereof, or a pharmaceutical composition as defined herein The present invention provides a use of a compound, or a pharmaceutically acceptable salt, hydrate or solvate thereof, as defined herein in the manufacture of a medicament for the treatment of a disease or condition ameliorated by osteogenesis.

In one embodiment, the disease or condition ameliorated by osteogenesisis selected from Paget's disease of bone and osteoporosis.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of antitumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN 107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and any one of the anti-tumour agents listed herein above.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination. In one embodiment, a combination refers to a combination product.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

Combination Product

In another aspect, the present invention relates to a combination product comprising a vitamin E derivative or a pharmaceutically acceptable salt or solvate thereof and a bisphosphonate or a pharmaceutically acceptable salt thereof.

In one embodiment, the bisphosphonate is selected from zoledronate, alendronate, pamidronate, etidronate, clodronate, tiludronate, neridronate, olpadronate, ibandronate, risedronate.

In another embodiment, the bisphosphonate moiety is a moiety according to general formula (IIIa) or (IIIb):

(IIIa)

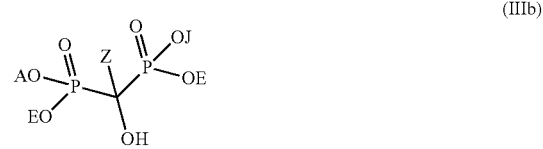

(IIIb)

wherein,

A, E, J and G are independently selected from hydrogen and $C_{1-6}$ alkyl;

Z is selected from hydrogen, halogen, hydroxyl, aryl, heteroaryl, and $C_{1-6}$ alkyl, wherein said aryl, heteroaryl and $C_{1-6}$ alkyl may optionally be substituted by one or more $R^z$ groups; and $R^z$ is selected from hydrogen, hydroxyl, halogen, COOH, CN, $C_{1-6}$ haloalkyl, $C_{1-6}$ haloalkoxy, $C_{3-6}$ cycloalkyl, $C_{1-6}$ alkyl and O—$C_{1-6}$ alkyl.

Suitably, the bisphonate and vitamin E derivative are present in a ratio (w/w) of about 10:1 to about 1:10, suitably about 5:1 to about 1:5, more suitably about 2:1 to about 1:2, more suitably about 1:1.

In one embodiment the combination product comprises/essentially consists of/consists of Bpp(OEt) and a vitamin E derivative selected from α-, β-, γ-, and δ-tocopherol and α, β-, γ-, and δ-tocotrienol. Suitably, the Bpp(OEt) and vitamin E derivative are present in about a 1:1 (w/w).

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of invention will vary depending on the nature of Q, T and L, or the nature of the variable groups in formula (I). Suitable processes for the preparation of encompassed are described non-exhaustively in the following general methods.

Synthesis of the claimed conjugates may be effected according general method 1 or 2 below.

General Method 1—Synthesis of Ester Linked Conjugates

The ester linked conjugates may be prepared by reacting an appropriate carboxylic acid containing the bisphosphonate moiety and an alcohol containing phytochemical to form an ester. Such esterification is sometimes referred to as Steglich esterification.

For example:

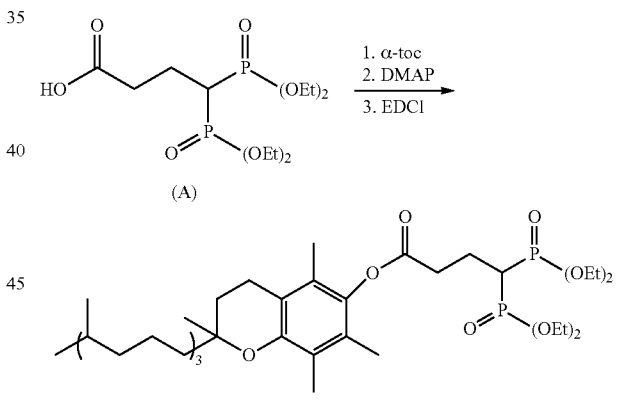

(A)

Suitably the reaction is carried in the presence of at least one coupling reagent. For example, the reaction may be conducted with 1-ethyl-3-(3-dimethylaminopropyl)carbodiimide (EDCl). The reaction may further comprise a co-coupling reagent, such as DMAP.

The reaction is typically carried out in an inert solvent, such as chloroform or dichloromethane.

The reaction is suitably carried out at a temperature ranging from about room temperature to about 70° C.

The phosphonate ester can subsequently be hydrolysed to the corresponding phosphonic acid by standard methods, such as treatment with bromotrimethylsilane (TMSBr).

Intermediate carboxylic acid (A) may be prepared from tetraethyl methylene bisphosphonate in five steps as shown below.

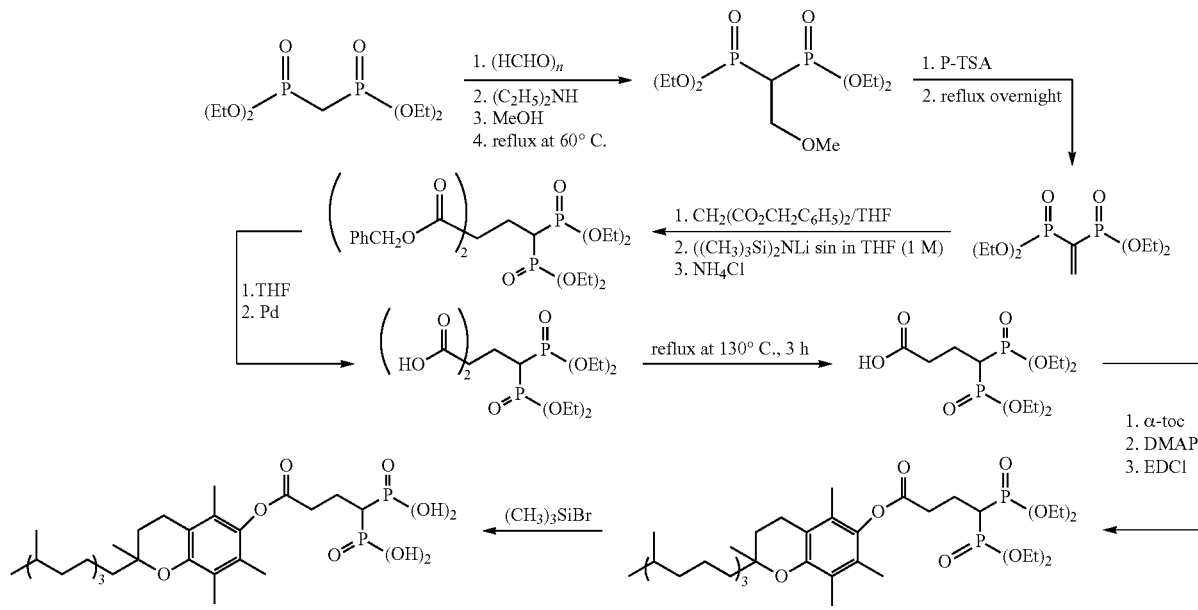

General Method 2—Synthesis of Ether Linked Conjugates

Formation of an ether linkage may proceed via base catalysed deprotonation of an appropriate hydroxyl containing phytochemical (such as alpha-tocopherol). The base used in this step could be any base commonly used in the art, for instance alkoxide or hydroxide bases (e.g sodium methoxide, sodium hydroxide). The alkoxide anion is then reacted with an appropriate halogenated carboxylic acid (for example 4-chloro butyric acid, 3-chloropropanoic acid, 2-chloroacetic acid or the respective bromides). Suitably an excess of a base and halogenated carboxylic acid is present.

The base catalysed dehydrohalogenation reaction may be conducted in any suitable solvent (e.g. DMF, toluene, alcohols) and may be carried out at elevated temperature.

For example:

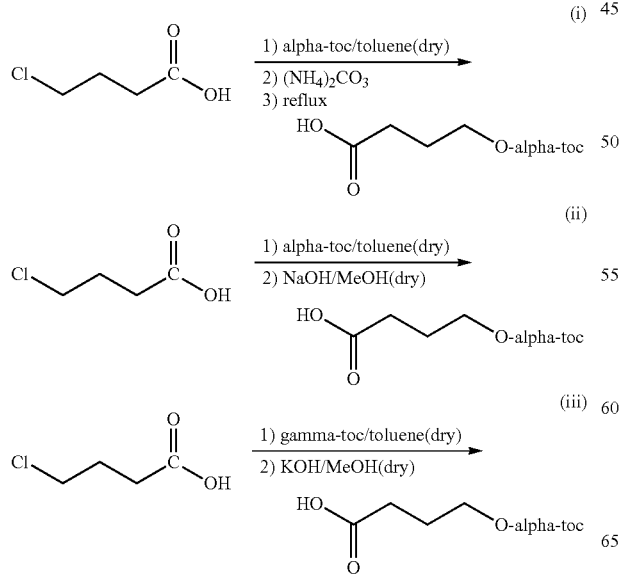

-continued

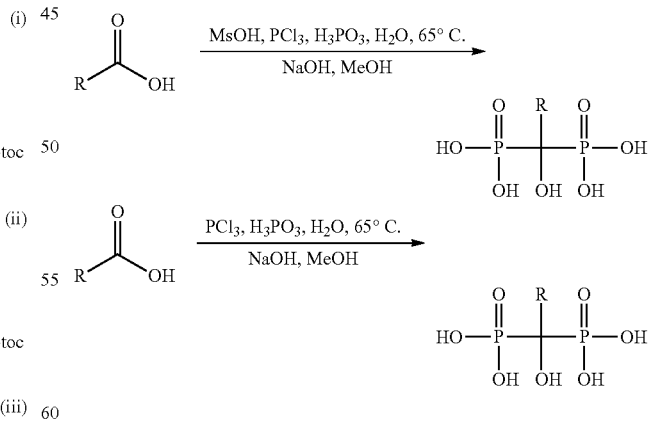

The resultant carboxylic acid is then converted to a bisphosphonate by reaction with phosphorus acid and phosphorus trichloride.

The reaction is suitably carried out in an inert atmosphere and at elevated temperature (e.g. about 65° C.). The reaction may be carried out in the presence or absence of solvent.

For example:

Examples

Chemistry

The compounds of the invention may be prepared using synthetic techniques that are known in the art (as illustrated by the examples herein).

In the following, ¹H-NMR spectroscopy was performed on a Bruker Avance 300 spectrophotometer which operates at 300.13 MHz, 75.47 MHz and 121.49 MHz for $^1$H, $^{13}$C and $^{31}$P nuclei respectively. Samples for NMR spectroscopy were prepared with dilution in either CDCl3, D$_2$O or DMSO. Concentrations varied between 10-100 mM.

Preparation 1: Tetraethyl (1-methylenemethoxy)methylene Bisphosphonate

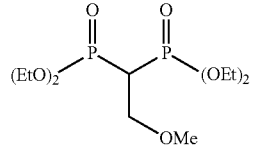

Tetraethyl methylene diphosphonate (20 mL, 80.70 mmol, 1.0 equiv.), paraformaldehyde, (12.12 g, 403.6 mmol, 5.0 equiv.), diethylamine (8.4 mL, 81.21 mmol, 1.0 equiv.) and 232 ml of methanol were added in a single-necked round bottom flask. The blurred mixture that incurred was heated at 60° C. for 90 min until transparence and was stirred for 15 h at room temperature. The solvent volume was shrunk, 40 ml of toluol were added and it was finally evaporated until dryness. A yellowish thick fluid was produced to which an additional 40 ml of toluol were added which together with evaporation under vacuum and complete eradication of methanol enabled the product isolation. (yield 32.72 g). $^1$HNMRδ(CDCl$_3$, ppm): 1.24 (12H, t, P—OCH$_2$CH$_3$); 2.46 (1H, tt, P$_2$CHCH$_2$OCH$_3$); 3.25 (3H, s, —OCH$_3$); 3.78 (2H, td, P$_2$CHCH$_2$OCH$_3$); 4.06 (8H, m, P—OCH$_2$CH$_3$).

Preparation 2: Tetraethyl Vinylidene Diphosphonate/Bisphosphonate

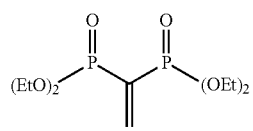

Catalytic quantity of p-tolouensoulfonic acid (0.1 g, 0.58 mmol) and 150 mL of dry toluol were added to Tetraethyl (1-methylmethoxy)methylene bisphosphonate (31.72 g). The sub-yellow transparent solution underwent stirring and boiling at 120° C. under Ar atmosphere for 12 h. Thebrownishtransparentsolutionthatincurredcooleddownandwasextracted with water (multiple aqueous phases with toluol). The organic phase was collected and dried with Na$_2$SO$_4$ and was followed by filtering and solvent evaporation. A thick yellowish liquid remained in the flask (yield 8.4 g)) $^1$HNMRδ(CDCl$_3$, ppm): 1.27 (12H, t, P—OCH$_2$CH$_3$); 4.05-4.15 (8H, m, P—OCH$_2$CH$_3$); 7.13 (2H, dd, P$_2$C=CH$_2$). $^{13}$CNMRδ(CDCl$_3$, ppm): 16.08 (4C, t, P—OCH$_2$CH$_3$); 63.00 (4C, d, P—OCH$_2$CH$_3$); 132.51 (1C, t, P—C—P); 149.04 (1C, s, —P$_2$C=CH$_2$). $^{31}$PNMRδ(CDCl$_3$, ppm): 22.73 (s).

Preparation 3: Tetra Ethyl [3,3 bis(benzyloxylocarbonyl) Propylideno Bisphosphonate

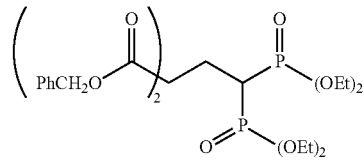

Tetraethyl vinylidene diphosphonate/bisphosphonate (8.54 g, 28.47 mmol, 1.0 equiv.), dibenzylomalonicether (7 mL, 28.51 mmol, 1.0 equiv.) and 130 mL dry THF were added in a double-necked round bottom flask. Di-(trismethylsilyl) amide salt of Lithium was added to the yellowish solution that incurred in tetahydrofuran solvent (1M) (0.53 mL, 2.821 mmol, 0.1 equiv.) and the solution was subjected to stirring for 1 h at room temperature. Subsequently, saturated aqueous solution of ammonium chloride (60 mL) was added and the mixture was extracted with dichloromethane 93×50 mL). The organic phase was dried with Na$_2$SO$_4$ and the solvent was evaporated under vacuum. The remaining yellowish thick liquid was diluted in a mixture of MeOH:CH$_2$Cl$_2$ (~5 mL, 2:98) and was purified with column chromatography using as an elution solvent a mixture of MeOH:CH$_2$Cl$_2$(2: 98). The solvent was evaporated and yielded 4.78 g of colorless thick liquid. $^1$HNMRδ(CDCl$_3$, ppm): 1.28 (6H, t, OCH$_2$CH$_3$); 1.29 (6H, t, OCH$_2$CH$_3$); 2.31-2.62 (3H, m); 4.02-4.16 (9H, m); 5.07 (4H, s, —OCH$_2$Ph); 7.18-7.23 (10H, m). $^{13}$CNMRδ(CDCl$_3$, ppm): 16.02 (2C, —OCH$_2$CH$_3$); 16.16 (2C, —OCH$_2$CH$_3$); 24.73 (1C, m, —CH$_2$CHP$_2$); 34.02 (1C, t, P—C—P); 49.81 (1C, t, —C(O)CHRC(O)); 62.58 (4C, m, —OCH$_2$CH$_3$); 67.03 (2C, —OCH$_2$Ph); 127.94 (4C, orthoC); 128.14 (2C, paraC); 128.31 (4C, metaC); 135.04 (2C, 1' onPh); 168.33 (2C, —O C(O)CH). $^{31}$PNMRδ(CDCl$_3$, ppm): 25.75 (s).

Preparation 4: Tetra Ethyl 3,3, Bis (Phosphono) Propylideno Bis (Carboxylic Acid)

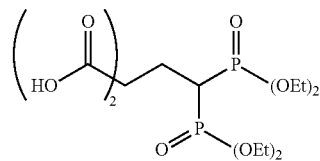

The tetra ethylo [3,3, bis)benzyloxycarbonyl) propylideno bisphosphonate (2.16 g, 3.68 mmol), was diluted in dry THF (30 mL) and Palladium 10% in active carbon (0.3 g, cat.) was added. The mixture was subjected to stirring under hydrogen atmosphere for 4 days. Subsequently it was filtered and washed with saturated aqueous solution of ammonium chloride (100 mL). The product was extracted with dichloromethane (6×100 mL) and dried with anhydrous Na$_2$SO$_4$. The solvent was evaporated under vacuum, diethylether was added and the creation of a yellowish solid was observed. Filtering and product drying followed (yield 0.64 g). $^1$HNMRδ(MeOD, ppm): 1.30 (12H, t, —P—OCH$_2$CH$_3$); 1.74 (2H, heptet, P$_2$CHCH$_2$CH—); 2.66 (1H, tt, P—CHRP); 3.26 (1H, t, —CH$_2$CH(CO$_2$H)$_2$); 4.07-4.19 (8H, m, P—O—C$\underline{H}_2$CH$_3$). $^{13}$C NMR δ(MeOD, ppm): 16.55 (2C, P—O—CH$_2$$\underline{C}$H$_3$); 16.68 (2C, P—O—$\underline{C}$H$_2$CH$_3$); 25.95 (1C, t, P$_2$CH$\underline{C}$H$_2$CH—); 35.01 (1C, t, P—$\underline{C}$HRP); 51.10 (1C, m, —$\underline{C}$H(CO$_2$H)$_2$); 64.45 (4C, dd, P—O—$\underline{C}$H$_2$CH$_3$); 171.84 (2C, —$\underline{C}$O$_2$H). $^{31}$P NMR δ(MeOD, ppm): 26.16 (s).

Preparation 5: Tetra Ethyl 4,4-bis(phosphono)-butanoic Acid [bpp(OEt)]

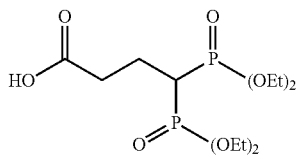

The tetraethylo 3,3, bis (phosphono)-propylideno bis) carboxylic acid (0.2 g, 0.495 mmol) was added to double-necked round bottom flask and under N$_2$ atmosphere, was heated at 130° C. for 3 h (in oil-bath of constant temperature). The product was isolated as a brown oil and the reaction yield was 0.174 g. $^1$HNMRδ(MeOD, ppm): 1.35 (12H, t, OCH$_2$C$\underline{H}_3$); 2.12-2.28 (2H, m, P$_2$CHC$\underline{H}_2$CH$_2$—); 2.62-2.67 (m,—CD$\underline{H}$CO$_2$H); 2.81 (1H, tt, —PC$\underline{H}$P—); 4.13-4.25 (8H, m, P—O—C$\underline{H}_2$CH$_3$). $^{13}$C NMR δ(MeOD, ppm): 16.57 (2C, P—O—CH$_2$$\underline{C}$H$_3$); 16.71 (2C, P—O—$\underline{C}$H$_2$CH$_3$); 21.82-22.10 (1C, m, P$_2$CH$\underline{C}$H$_2$CH$_2$—); 32.53-33.07 (1C, m, P$_2$CHCH$_2$$\underline{C}$H$_2$CO$_2$H); 35.87 (1C, t, P—$\underline{C}$HR—P); 64.07-64.36 (4C, m, —P—O—$\underline{C}$H$_2$CH$_3$); 175.85 (1C, —$\underline{C}$O$_2$H). $^{31}$PNMRδ(MeOD, ppm): 26.73 (s).

Example 1: α-Tocopheryl Bisphosphonic Ester (α-Toc-bppOEt)

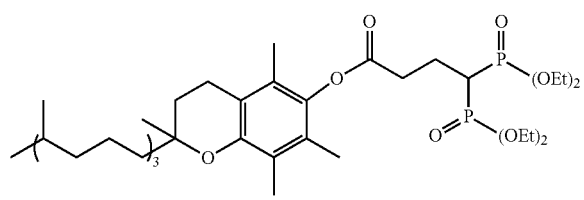

In a double-necked spherical flask containing tetra-ethyl-4,4 bis (phosphono)-butanoic acid (0.07 g, 0.197 mmol, 1.0 equiv.) in 10 ml of dry dichloromethane were added α-tocopherol (0.1 g, 0.233 mmol, 1.2 equiv.) and 4-(N,N-dimethylamino)pyridine (0.005 g, 0.04 mmol, 0.2 equiv.). Reacting molecule addition and stirring took place at 0° C., under nitrogen atmosphere. Subsequently, EDCl (0.045 g, 0.235 mmol, 1.2 equiv.) was added and the mixture was allowed to reach gradually to 25° C. The reaction was completed after stirring at room temperature for 48 hrs. The mixture was extracted with water (3×20 mL), the organic phase was dried with anhydrous Na2SO4 and the solvent was evaporated under vacuum. The oily substance that stayed behind was dissolved in a mixture of MeOH: CH2Cl2 (~1 mL, 3: 100) and purified with column chromatography using as initial elution solvents a mixture of MeOH: CH2Cl2 (3: 100) followed by methanol. The solvent was evaporated and yielded 0.2 g colorless thick liquid. $^1$H, $^{13}$C and $^{31}$P-NMR spectra are highly comparable to those of tetra ethyl 4,4-bis(phosphono)-butanic acid with the additional peaks corresponding to the methyl groups of the chromanol ring. Notably, in the $^{31}$P-NMR spectrum only one peak is recorded instead of two, as it would be expected.

Example 2: γ-tocopheryl bisphosphonic ester (γ-toc-bppOEt)

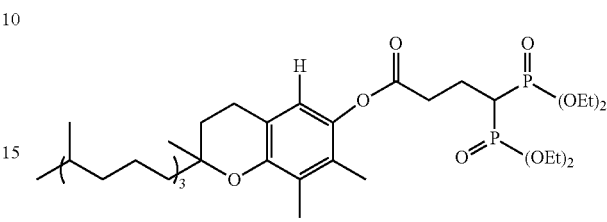

Figure 12A:
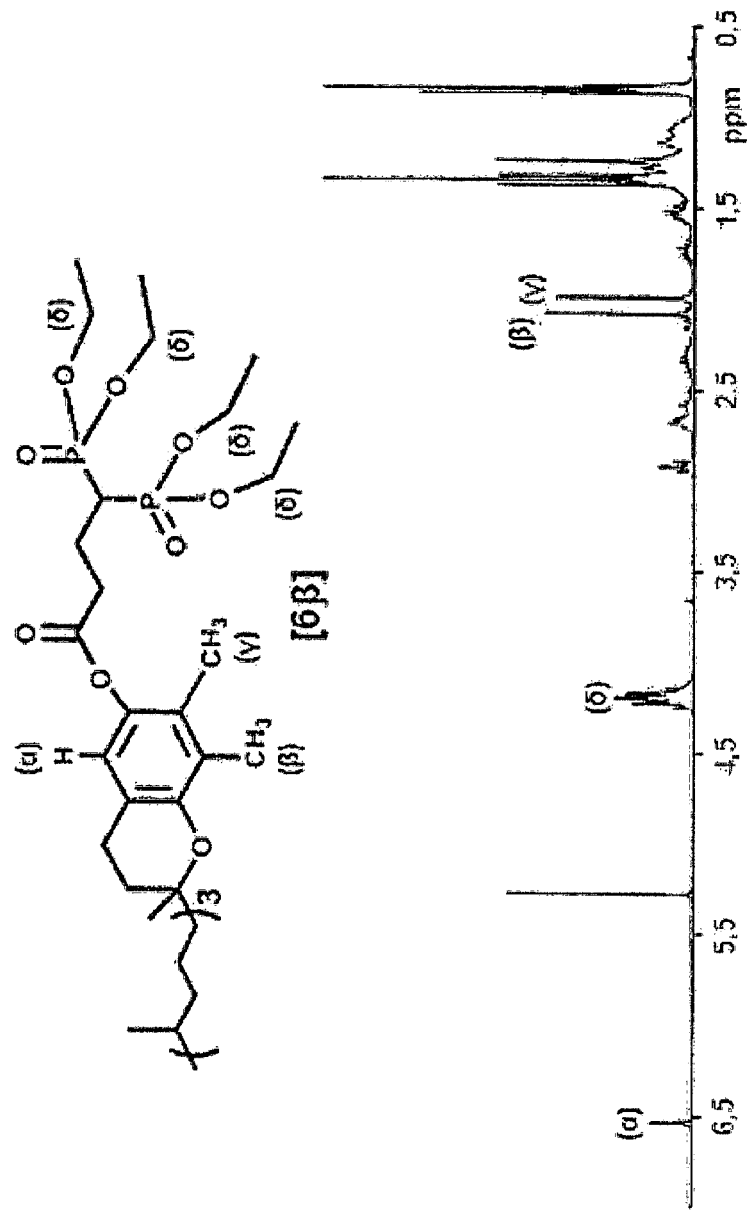
FIG. 12 shows A $^1$H-NMR spectrum, B $^{13}$C-NMR spectrum and C $^{31}$P-NMR spectrum for gamma-tocopheryl bisphosphonic ester (γ-toc-bppOEt; example 2).
Figure 12B:
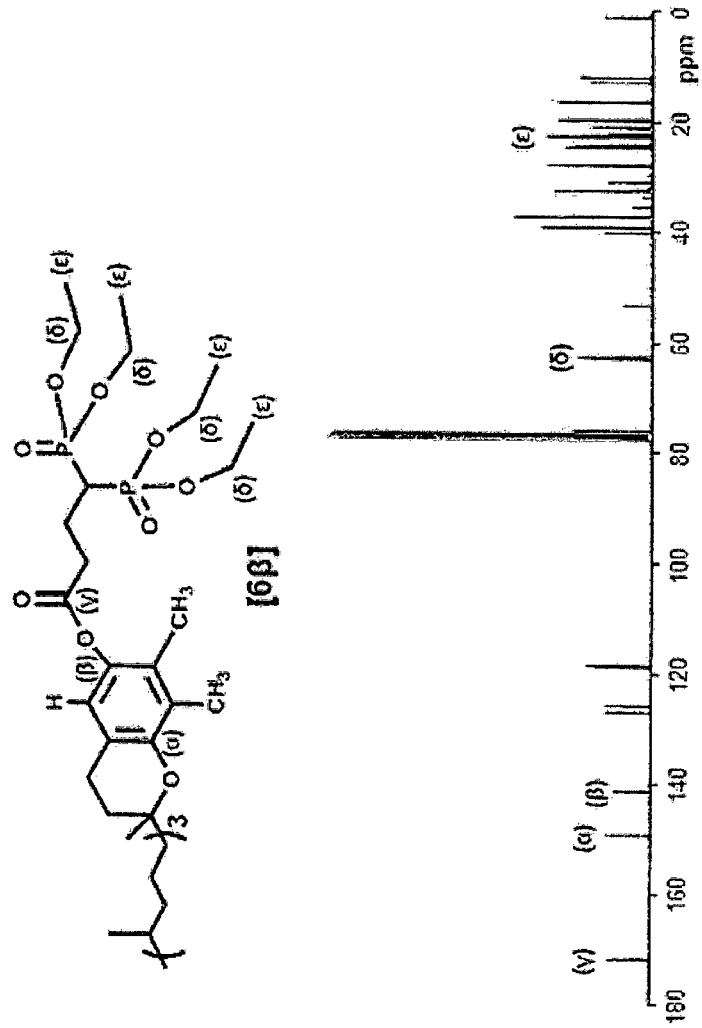
Figure 12C:
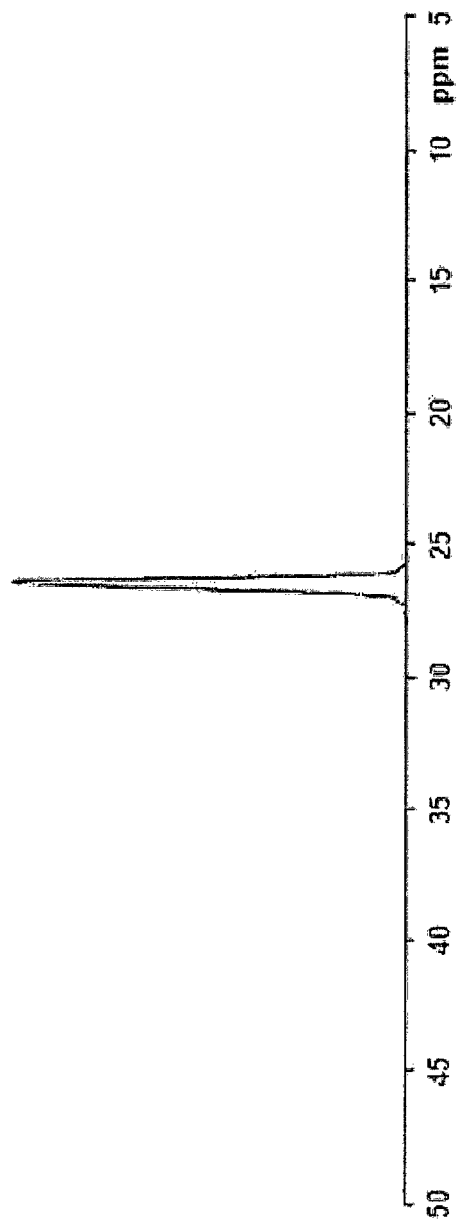

This molecule was synthesized with the same methodology as α-toc-bppOEt (0.05 γethyl-4,4 bis(phosphono)-butanoic acid, 0.07 gγ-tocopherol, 0.004 γ4-(N,N-dimethylamino)pyridine, and 0.032 g EDCl. The reaction yield was 0.1 g. FIG. 12 shows A $^1$H-NMR spectrum, B $^{13}$C-NMR spectrum and C $^{31}$P-NMR spectrum for gamma-tocopheryl bisphosphonic ester.

Example 3: δ-Tocopheryl Bisphosphonic Ester (5-toc-bppOEt)

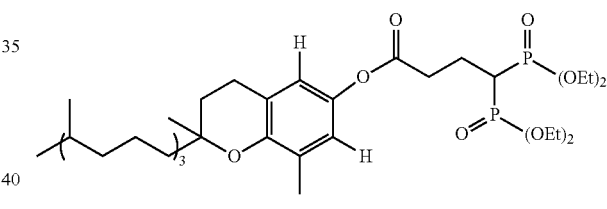

This molecule was synthesized with the same methodology as α-toc-bppOEt. The reaction yield was 0.2 g (it features similar chemical transitions with α-toc-bppOEt except with a double peak due to the aromatic protons at 6.88 ppm).

Example 4: γ-tocotrienyl Bisphosphonatic Ester (γ-tot-bppOEt)

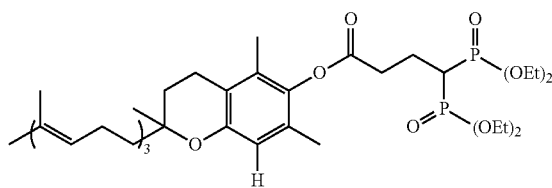

This molecule was synthesized with the same methodology as α-toc-bppOEt. The reaction yield was 0.1 g (it featured similar chemical transitions with γ-toc-bppOEt with a peak due to the aromatic proton at 6.55 ppm).

Example 5: Farnesyl Bisphosphonic Ester (farn-bppOEt)

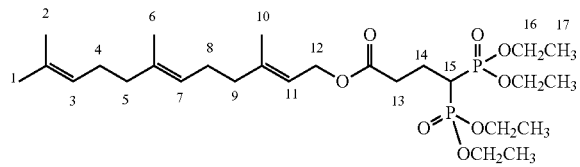

This molecule was synthesized with the same methodology as α-toc-bppOEt. The reaction yield was 0.2 g. $^1$HNMRδ(CDCl$_3$, ppm): 5.21 (t, 1H, H11); 5.10 9 (s, 2H, H3, H7); 4.61 (d, 2H, H12); 4.25 (p, 8H, H16); 2.20 (t, 2H, H13); 1.89 (s, 8H, H4, H5, H8, H9); 1.75 (s, 9H, H1, H6, H10); 1.63 (p, 5H, H2, H14); 1.42 (h, 1H, H15); 1.30 (t, 12H, H17).

Example 6: Phytyl Bisphosphonic Ester (phyt-bppOEt)

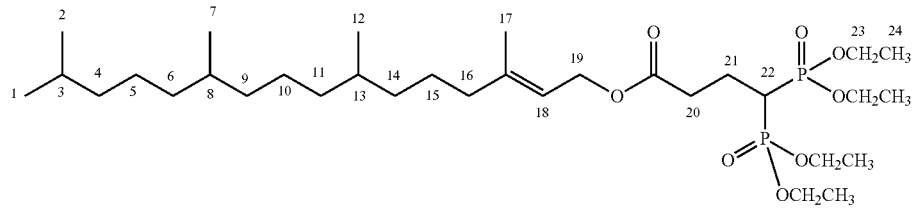

This molecule was synthesized with the same methodology as α-toc-bppOEt. The reaction yield was 0.2 g. $^1$H NMR δ(CDCl$_3$, ppm): 5.25 (t, 1H, H18); 4.50 (d, 2H, H19); 4.20 (p, 8H, H23); 2.30 (t, 2H, H20); 1.90 (t, 2H, H16); 1.77 (s, 3H, H17); 1.70-1.45 (m, 6H, H21, H3, H8, H13, H22); 1.35-1.20 (m, 28H, H15, H24, H4, H5, H6, H9, H10, H11, H14); 0.90 (dd, 12H, H7, H12, H1, H2).

Example 7: α-tocopheryl Bisphosphonic Acid (α-toc-bppOH)

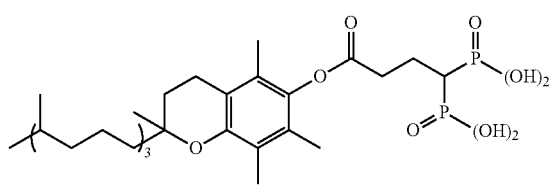

In a solution of α-toc-bppOEt (0.1 g, 0.130 mmol, 1.0 equiv.) in a mixture of CCl$_4$/CHCl$_3$ 1:1 (3 mL, dry), trimethylobromosilane (0.5 mL, 0.58 g, 3.79 mmol, 29 equiv.) was added and the mixture underwent stirring for 24 hrs under argon atmosphere. Consequently 5 mL of water were added and the mixture was extracted with CHCl$_3$. The organic phase was dried with anhydrous Na$_2$SO$_4$, the solvent was evaporated under vacuum and yielded 0.08 g brown oily substance which featured similar chemical transitions with α-toc-bppOEt differing only in the absence of proton beams from the esteric moieties of the bisphosphonate.

Example 8: γ-tocopheryl Diphosphonic Acid (γ-toc-bppOH)

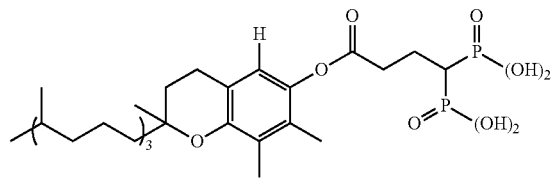

For the synthesis of this molecule the methodology developed for the synthesis of α-toc-bppOH was implemented. The reaction yield was 0.05 g (it features chemical transitions similar to those of γ-toc-bppOEt differing only in the absence of the proton peaks of the esteric moieies of the bisphosponate).

Example 9: δ-tocopheryl Bisphosphonic Acid (δ-toc-bppOH)

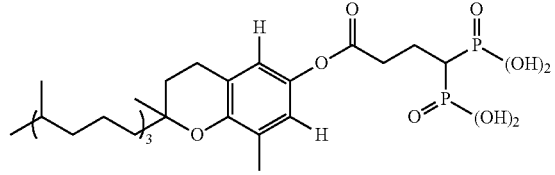

The methodology of the synthesis of α-toc-bppOH has been applied. The reaction yield was 0.06 g (it features similar chemical transitions with δ-toc-bppOEt with the difference that the peaks of protons at the esteric moieties of the bisphosphonate are absent).

Example 10: γ-tocotrienol Bisphosphonic Acid (γ-tot-bppOH))

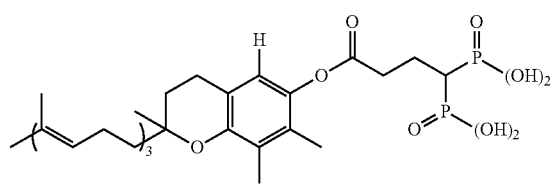

The methodology developed for the synthesis of α-toc-bppOH has been followed for the synthesis of this molecule.

The reaction yield has been 0.05 g (chemical transitions similar to γ-tot-bppOEt have been presented with the sole difference being the absence of the proton peaks of the esteric moieties of the biphosphonate).

Example 11: Farnesyl Bisphosphonic Acid (farn-bppOH)

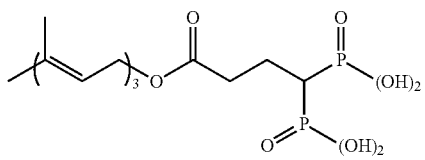

The methodology developed for the synthesis of α-toc-bppOH has been followed for the synthesis of this molecule. The reaction yield has been 0.08 g (chemical transitions similar to farn-bppOEt have been observed with the sole difference being the absence of the proton peaks of the esteric moieties of the biphosphonate).

Example 12: Phytyl Bisphosphonic Acid (phyt-bppOH)

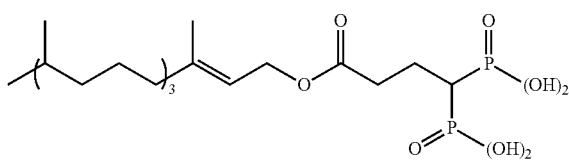

The methodology developed for the synthesis of α-toc-bppOH has been followed for the synthesis of this molecule. The reaction yield has been 0.07 g (chemical transitions similar to phyt-bppOEt, have been observed with the sole difference being the absence of the proton peaks of the esteric moieties of the biphosphonate).

Biology

I. Antiproliferative and Proapoptotic Efficacy in Metastatic Breast Cancer Lines Ii. Cell Viability Immortalised osteolytic metastatic breast cancer cell lines, a) hormone-dependent MCF-7 and b) hormone refractory MDA-MB231, together with the daughter line MDA-MB231TXSA were incubated with 5 gradual concentrations of compounds of the invention as described below. Cell viability was assessed with the crystal violet colorimetric assay and $IC_{50}$s were evaluated.

Crystal Violet (CV) Colorimetric Assay

Medium was removed from cell cultures and cells were fixed with 4% v/v formaldehyde for 5 mins at room temperature. Formalin was then removed and CV added for 10 mins at room temperature followed by several washes with $dsH_2O$. Samples were allowed to dry overnight. The following day, 10% acetic acid was added for 15 mins and optical density at 620 nm was measured. Optical densities versus compound concentrations were plotted in graphs and $IC_{50}$s estimated by linear regression analysis using the WorkOut (VictorX4) software.

MCF-7, MDA-MB231 and MDA-MB231TXSA cells were seeded in 96-well-plates and allowed to attach overnight. The following day media were replaced with fresh media containing the following compounds: Both free tetraethyl methylbisphosphonate (bpp(OEt)) and bpp(OEt) in 1:1 combination with the free chromanol and the biphosphonate conjugates were tested at 5 gradual concentrations of: 0.02, 0.04, 0.06, 0.08 and 0.1 mM.

Cells were cultured in the presence of the compounds for 72 hrs and viability was assessed on day 3 by crystal violet assay. The cell lines were selected for their high bone metastatic potential. The fluorescently transfected line MB231TXSA, derived from line MB231 is also used in animal studies (WP7).

Indicative $IC_{50}$ values are given in the tables below.

Exp.1

| | IC50 values | | |
|---|---|---|---|
| | MB231-TXSA | MB231 | MCF-7 |
| γ-toc | 0.0974 | 0.3125 * | 0.439 * |
| γ-toc-bpp(OEt) | 0.0793 | 0.1245 | 0.1145 |
| γ-toc-bpp(OH) | 0.092 | 0.1716 | 0.3027 * |
| γ-toc + bpp(OEt) 1: | 0.0697 | 0.1904 * | 0.1363 * |
| bpp(OEt) | 0.4414 | 0.1057 | 0.1066 |

Exp.2

| | IC50 values | | |
|---|---|---|---|
| | MB231-TXSA | MB231 | MCF-7 |
| γ-toc | 0.2326 | 0.0557 | 0.1277 |
| γ-toc-bpp(OEt) | 0.1888 * | 0.0497 | 0.0815 |
| γ-toc-bpp(OH) | 0.1825 * | 0.0662 | 0.0651 |
| γ-toc + bpp(OEt) 1:1 | 0.4083 * | 0.0791 | 0.1065 |
| bpp(OEt) | 0.1288 | 0.2425 | 0.1426 * |

Exp.3

| | IC50 values | | |
|---|---|---|---|
| | MB231-TXSA | MB231 | MCF-7 |
| α-toc | 0.1368 | 0.1031 | 0.0547 |
| α-toc-bpp(OEt) | 0.0981 | 0.1283 | 0.1523 * |
| α-toc-bpp(OH) | 0.0888 | 0.0616 | 0.3508 * |
| α-toc + bpp(OEt) 1:1 | 0.2021 | 0.0607 | 0.0907 |
| bpp(OEt) | 0.1355 | 0.0742 * | 0.3646 * |

Exp.4

| | IC50 values | | |
|---|---|---|---|
| | MB231-TXSA | MB231 | MCF-7 |
| α-toc | 0.08868 | 0.13124 * | 0.05447 |
| α-toc-bpp(OEt) | 0.073 | 0.28082 | 0.07677 |
| α-toc-bpp(OH) | 0.07589 | 0.23833 | 0.06414 |
| α-toc + bpp(OEt) 1:1 | 0.10198 | 0.12239 | 0.25349 * |
| bpp(OEt) | 0.1794 | 0.71027 * | 1.97796 * |

Note:
* denotes $EC_{50}$ value

Figure 11:
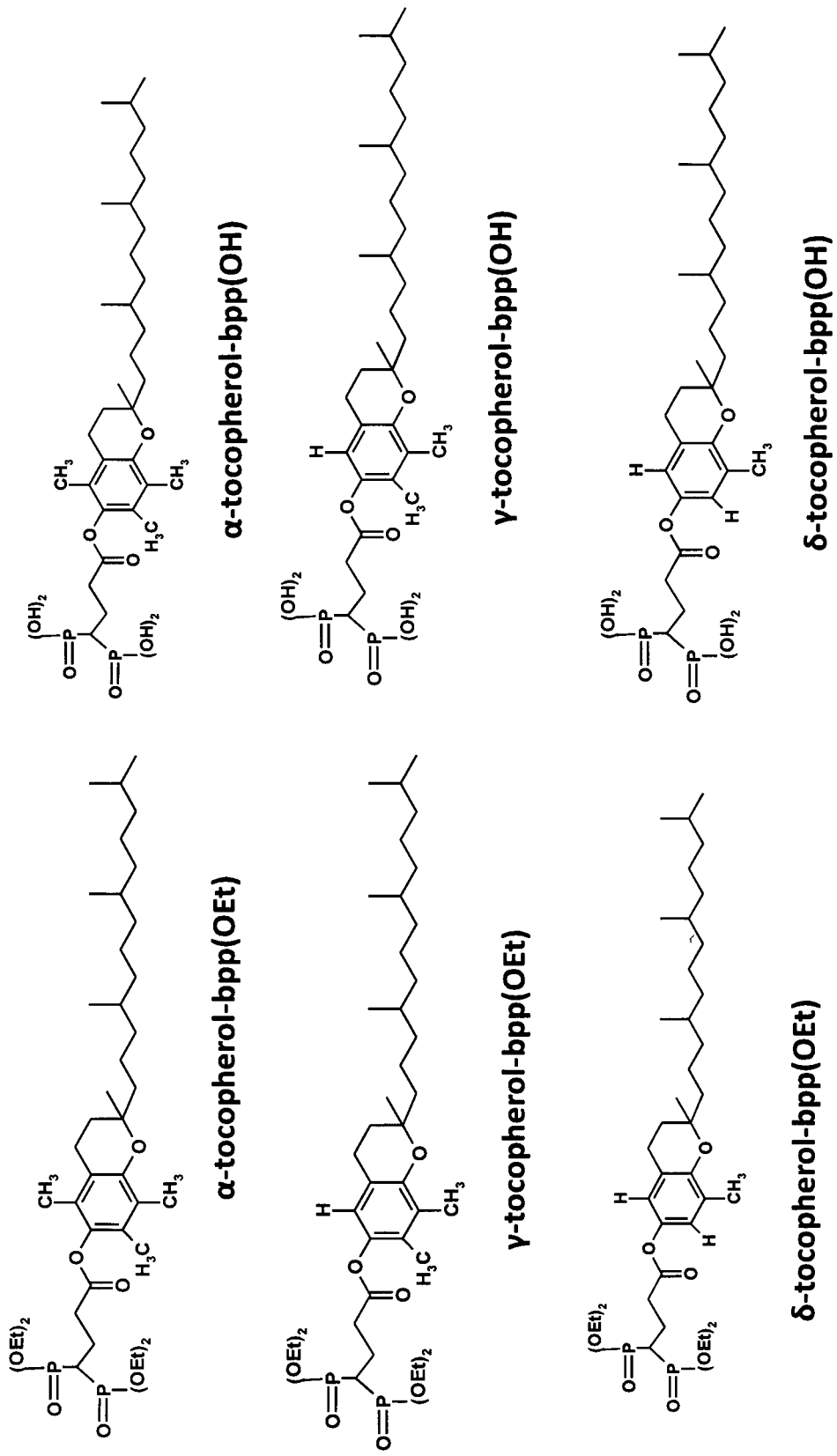
FIG. 11 shows the structures of compounds disclosed herein and their abbreviations.

The viability assays and $IC_{50}$s showed that the compounds α-tocopherol-bpp(OEt), α-tocopherol-bpp(OH), α-tocopherol+bpp(OEt) (1:1), γ-tocopherol-bpp(OEt), γ-tocopherol-bpp(OH) and γ-tocopherol+bpp(OEt) (1:1)(see FIG. 11) reduced cell viability.

The antiproliferative activity of γ-tocopherol was increased upon esterification in the γ-tocopherol-bpp(OEt) and γ-tocopherol-bpp(OH) compounds. Furthermore, the antiproliferative activity of bpp(OEt) was increased in the esterified compounds α-tocopherol-bpp(OEt), α-tocopherol-bpp(OH), γ-tocopherol-bpp(OEt), γ-tocopherol-bpp(OH) as well as in the mixtures α-tocopherol+bpp(OEt) (1:1) or γ-tocopherol+bpp(OEt) (1:1).

Furthermore, it was shown that cell viability on both breast and prostate cancer metastatic cell lines was inhibited in a dose-dependent manner by both free γ-Tocotrienol and BP-γ-Tocotrienol conjugate, whereas the free BP((bpp(OEt)) was without effect (see FIG. 1).

Compounds with statistically significant decrease in viability were further examined to determine whether their effect was due to induced apoptosis based on morphologic criteria in DAPI-stained cells. These experiments demonstrated increased apoptosis which was further quantified with the measurement of caspase-3 enzymatic activity in an assay employing a fluorogenic substrate. Pro-apoptotic efficacies were compared using two-way analysis of Variance (ANOVA) followed by Bonferroni post-tests.

Iii. Proapoptotic Efficacy in Metastatic Breast Cancer Lines

Cell Fixation and DAPI Staining

Figure 2:
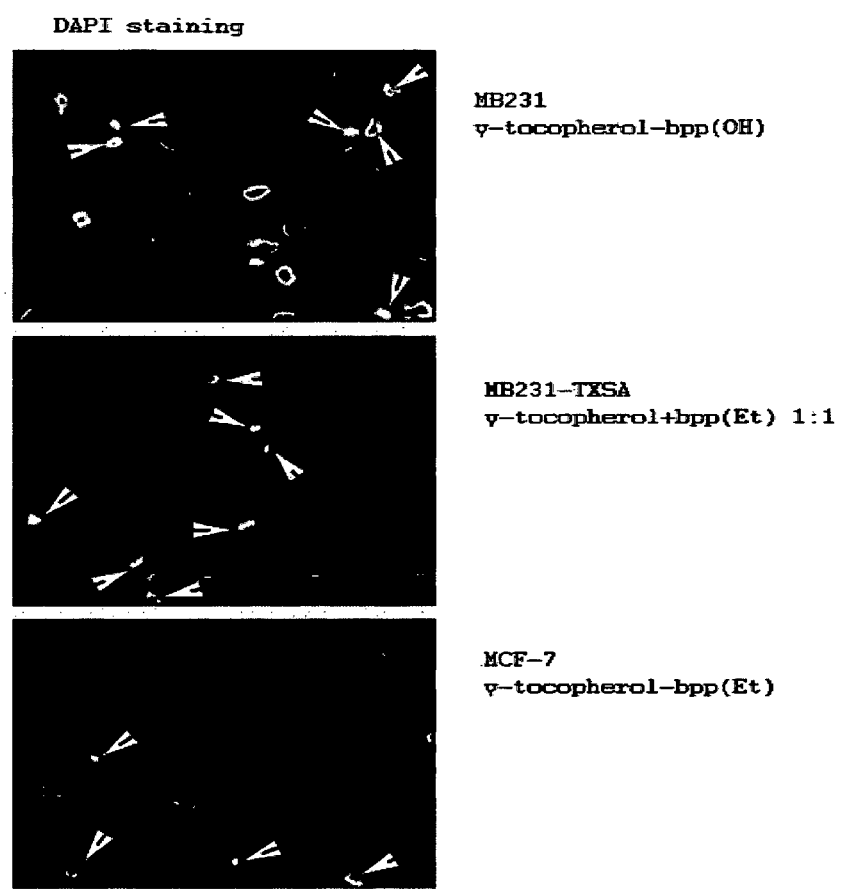
FIG. 2 shows indicative fluorescence microscopy digital images of nuclear DAPI staining. Apoptotic nuclei are indicated by arrowheads and were classified based on the presence of condensed chromatin or nuclear fragmentation.

Cells were grown on glass coverslips and treated with $IC_{50}$ concentrations of compounds of the invention that showed statistically significant decrease in viability in the cell viability assay. Growth medium was removed and cells were fixed with 4% v/v formaldehyde in PBS for 5 mins at room temperature. Fixed cells were washed once with PBS and incubated with 1 μg/ml DAPI in PBS for 20 mins at 37° C. Rinsed with PBS and mounted in mounting medium. Coverslips were sealed on glass slides and examined for the presence of apoptotic cells by fluorescence microscopy (see FIG. 2).

DAPI staining of cell nuclei showed increased numbers of apoptotic nuclei (condensed chromatin, fractured nuclei) in cell cultures treated with γ-tocopherol-bpp(OH) or γ-tocopherol+bpp(OEt) (1:1).

Caspase-3 Enzymatic Activity Assay

Cells were grown in 12 well-plates in the presence of $IC_{50}$ concentrations of compounds of the invention or culture medium with 0.1% v/v ethanol as control and were washed with PBS and incubated with lysis buffer for 15 mins at 4° C. Lysates were centrifuged at 15000 g. 20 μl of each lysate suspension was incubated with 100 μl of protease buffer containing 10 μM of fluorescent substrate zDEVD-AFC (3 samples/lysate) for 4 hrs at room temperature. Caspase-3 enzymatic activity was measured every 1 hr by fluorescence with excitation at 405 nm and emission at 515/30 nm.

Analysis of Caspase-3 Activity Results

Figure 3:
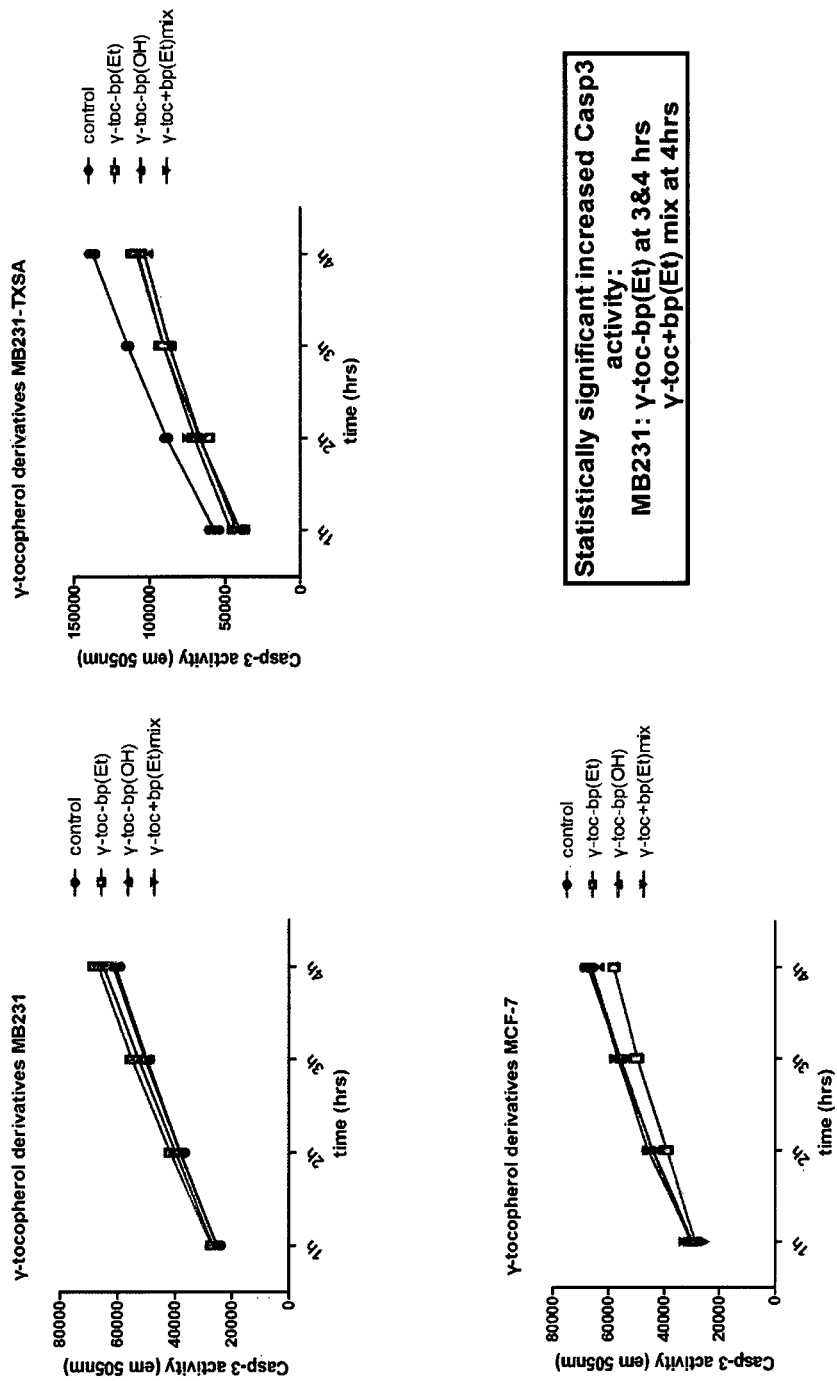
FIG. 3 shows apoptotic Caspase-3 enzymatic activity vs time for the identified compounds.
Figure 3:
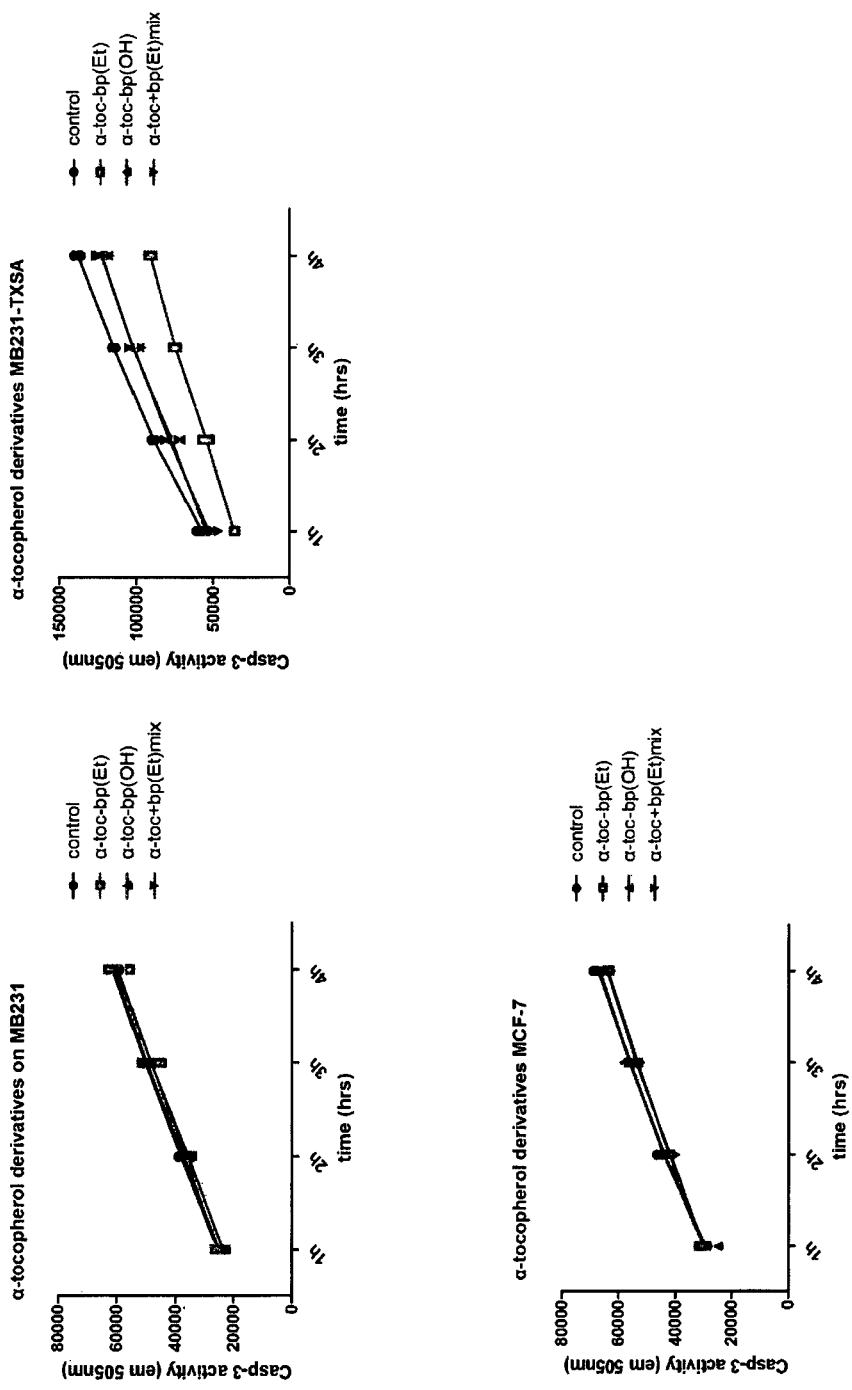

Fluorescence measurements were plotted in graphs against time and were statistically analysed by two-way ANOVA followed by Bonferroni post-tests to identify statistically significant apoptotic activities of compounds of the invention (see FIG. 3).

The Caspase-3 assays showed that of the six compounds of the invention: (α-tocopherol-bpp(OEt), α-tocopherol-bpp(OH), α-tocopherol+bpp(OEt) (1:1), γ-tocopherol-bpp(OEt), γ-tocopherol-bpp(OH) and γ-tocopherol+bpp(OEt) (1:1)) which showed decreased cell viability in the CV assay, only the compounds γ-tocopherol-bpp(OEt) and γ-tocopherol+bpp(OEt) (1:1) had statistically significant pro-apoptotic activities in one breast cancer cell-line the MB231. The increased Caspase-3 activity was not statistically different between the two compounds but the effect of γ-tocopherol-bpp(OEt) was present at an earlier time-point (at 3 hrs) compared to the γ-tocopherol+bpp(OEt) (at 4 hrs). Therefore, the pro-apoptotic efficacy of the two compounds may be attributed to the bpp(OEt) group and its esterification with γ-tocopherol in the γ-tocopherol-bpp(OEt) compound may facilitate its faster penetration into the cells where more rapidly exerts its action compared to γ-tocopherol+bpp(OEt). γ-tocopherol-bpp(OH) did not show significant pro-apoptotic activity in the Caspase-3 assay.

II. Investigation of the Effects and Mechanisms of Actions of Compounds of the Invention on Osteoclast Differentiation and Bone Resorption In Vitro Osteoclastogenesis Assays Human peripheral blood mononuclear cells (PBMCs) and the RAW264.7 murine monocytic cell line were differentiated into osteoclast-like cells in the presence of RANKL plus M-CSF and have been used as model systems of osteoclastogenesis. Osteoclast-like cells, from Giant Cell Tumours (GCT) of bone specimens from three independent donors were used to investigate the effect of compounds of the invention on the bone resorbing activity of mature osteoclasts.

Human Peripheral Blood Mononuclear Cells (PBMCs)

Human PBMCs were isolated from normal healthy donors isolated from the buffy coats acquired from the local Red Cross Blood Service. The cells were diluted in Hanks Balanced Salt Solution (HBSS) and separated by gradient centrifugation with Lymphoprep™. Isolated cells were resuspended in α MOD, 10% FCS, L-glutamine (2 mM), Hepes (20 mM), supplemented with M-CSF (25 ng/ml), $1\alpha,25(OH)_2$ vitamin D3 (10 nM) and dexamethasone (10 nM) and plated into 96-well plates containing whale dentine slices, for the bone resorption assay or directly into wells for TRAP staining. The following day, media were removed and replaced with media as above, supplemented with RANKL (100 ng/ml) in the presence or absence of increasing concentrations of compounds of the invention. Medium and treatments were replaced every three days.

RAW 264.7 Cells

Cells were cultured in 96-well plates at a density of $1 \times 10^4$ cells/well in DMEM medium with 10% FCS, L-glutamine (2 mM) and Hepes (20 mM). Cells were allowed to attach for 4 hrs before treatment with RANKL (50 ng/ml) in the presence or absence of increasing concentrations of compounds of the invention as above. Medium and treatments were replaced on day three and TRAP activity determined on day 5. The overall number of viable cells were determined by crystal violet staining.

Giant Cell Tumour of Bone (GCT)

To determine the effect of compounds of the invention on bone resorbing activity of mature osteoclast, cultured cells isolated from primary human Giant Cell Tumours of bone specimens were used. These cells were plated on whale dentine slices in 96-well plates at a density of 1×105/well and treated for 5 days with increasing concentrations of compounds of the invention. Medium and treatments were replaced on day three and pit formation determined on day 5.

TRAP Staining of Osteoclast Cultures

Osteoclast cultures established by the differentiation of RAW264.7 cells in wells were fixed and stained for tartrate resistant acid phosphatase (TRAP) as recommended by the manufacturer on days 4 and 5. TRAP positive cells were visualised by light microscopy and images taken with a digital camera.

Pit Formation Assay

Whale dentine slices will be washed in extran, rinsed with distilled water, washed in 70% ethanol and dried overnight. The dentine slices mounted on stubs, carbon-coated and visualised on a Philips XL-20 scanning electron microscope, (SEM) as previously described. Images will be analysed using ImageQuant software and the area of resorption determined for each dentine slice (quadruplicate dentine slices for each treatment). Results are expected to be average resorption area +/− standard errors of the mean (SEM) and the significant differences between treatments will be determined using Students t-tests (2-tailed, unpaired).

Results

Figure 4:
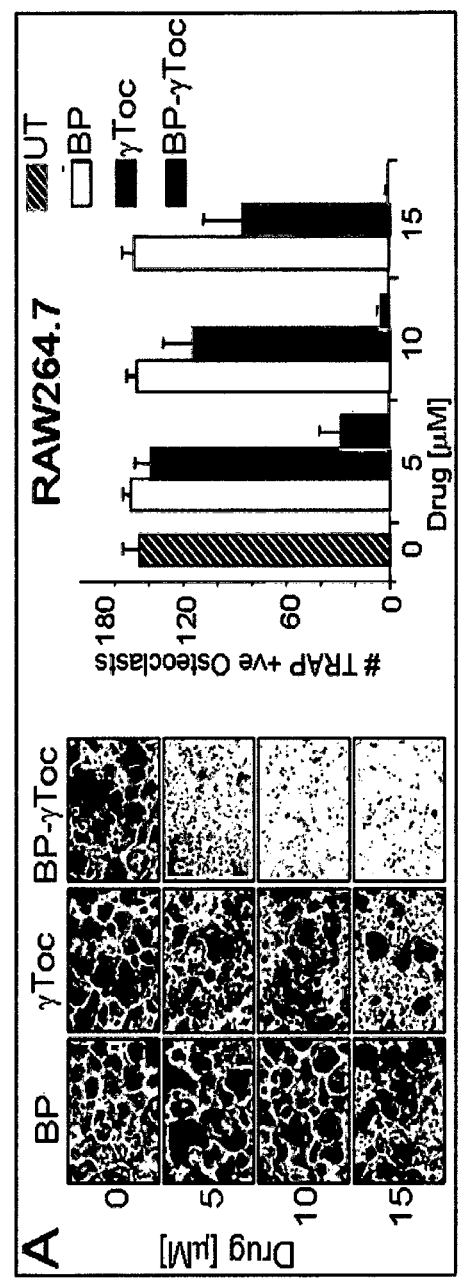
FIG. 4 shows TRAP positive cells visualised by light microscopy.

Raw264.7 was successfully differentiated into osteoclasts the efficacy of γ-tocopherol and bpp(OEt) to inhibit osteoclastogenesis of Raw264.7 was examined. The results showed that γ-tocopherol increased osteoclastogenesis at concentrations 1 μg/ml and 201 μg/ml. On the contrary, increasing concentrations of bpp(OEt) inhibited Raw264.7 osteoclastogenesis. Therefore, the compound bpp(OEt) did not have antiproliferative/proapoptotic effect in metastatic breast cancer cell-lines but inhibited osteoclastogenesis in a dose-dependent manner (see FIG. 4).

Figure 5:
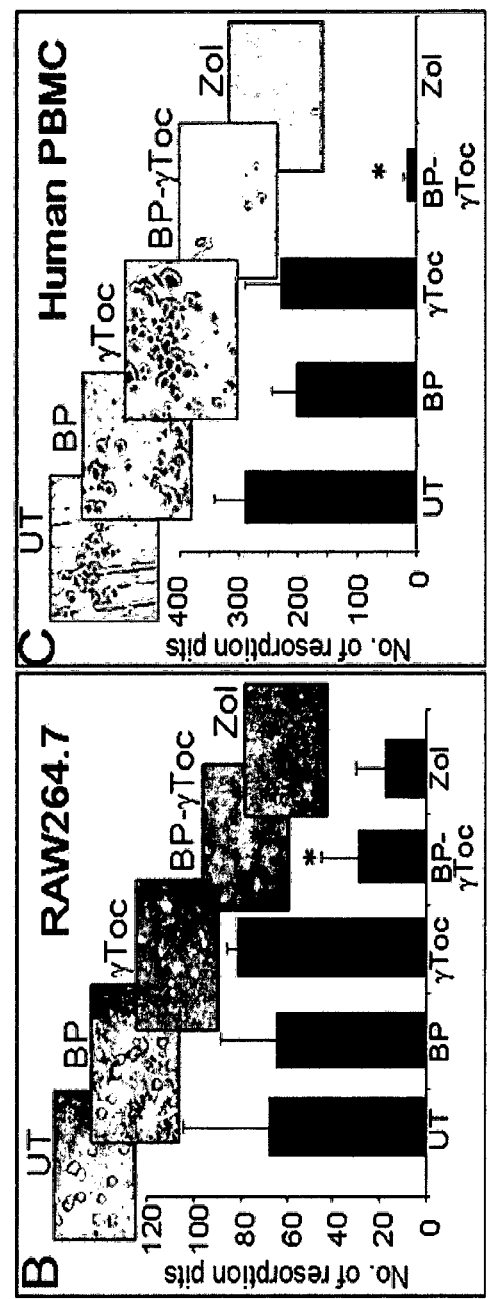
FIG. 5 shows the visualisation of resorption pits when whale dentine pre-loaded with the identified compounds and incubated with RAW264.7 (B) and Human PBMC (C). Zoledronic acid was used as control.

In a separate experiment, pre-loaded bone slices (whale dentine) or commercial forms of hydroxyapatite (osteologic slides) with either free γ-tocopherol (γToc) or γ-tocopherol-bpp(OEt) (BP-γToc) and then washed away unbound drug. BP-γToc, but not free γToc, selectively bound the substrate and inhibited resorption to an extent comparable with that seen with zoledronic acid (Zol), which was used as a control (FIG. 5).

This observation clearly demonstrates that BP-γToc binds bone mineral selectively through the bisphosphonate moiety and retains the ability to inhibit osteoclast differentiation and/or resorptive activity.

The doses of compound that inhibited bone resorption had no effect on the viability of either PBMCs or RAW264.7 cells, indicating that the drug-mediated effects on osteoclast function were not due to cytotoxicity but were specific for osteoclast differentiation and/or resorptive activity. In addition, both free γToc and BP-γToc inhibited bone resorption by already mature osteoclasts isolated from human Giant Cell Tumours (GCT) of bone.

The effect of γToc on osteoclast function has not previously been described and our results demonstrate for the first time that, not only does free γToc have an inhibitory effect on the differentiation and activity of osteoclasts, but more importantly, the BP-conjugated compound BP-γToc binds selectively to bone mineral and retains the inhibitory activity on osteoclast differentiation and bone resorption.

It is important to note that the free bisphosphonate used for these studies was selected on the basis that it has minimal anti-resorptive activity, despite having high affinity for bone as we have shown. Therefore, any observed effect of the conjugated compounds can be attributed to the vitamin E component.

III. Investigation of the Effects and Mechanisms of Actions of Compounds of the Invention on Osteoblast Maturation The effect of free γToc and BP-γToc treatment on osteoblast function, using mineralized bone nodule-forming primary human osteoblast cultures was investigated.

Figure 6:
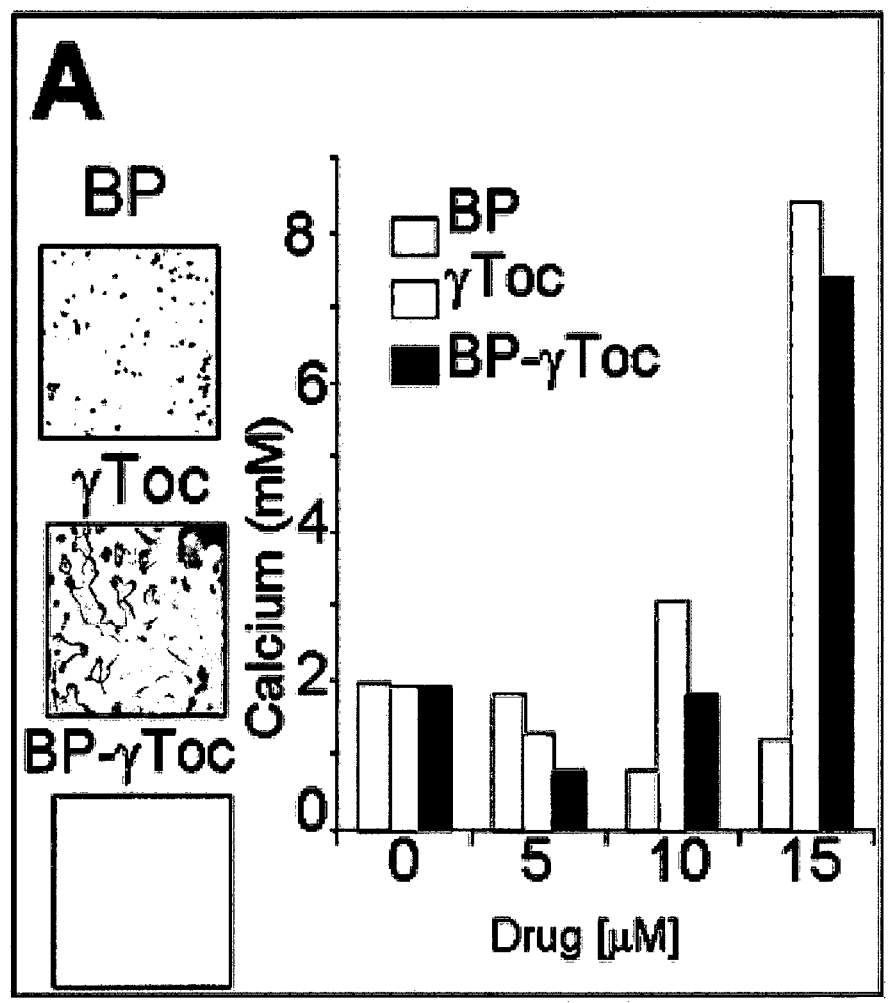
FIG. 6 shows that compounds disclosed herein increase mineralization by human osteoblasts under osteo-inductive conditions, as shown by alizarin red staining and by quantification of matrix-associated extracellular calcium.

Osteoblasts harvested from human donors at the time of joint replacement surgery were cultured up to 15 days in serum-containing medium under osteo-inductive conditions. Both the free γToc and BP-γToc progressively increased matrix-containing mineralized nodules in osteoblast cultures when compared to osteoblasts treated with the free BP, as assessed by an increase in alizarin red staining and an in increase in calcium in the cell layer (FIG. 6).

IV. Animal Models

Calvarial Organotypic Bone Growth Assay

An exvivo model of cultured mouse neonatal calvariae to assess bone anabolic activity of each compound was performed as previously described by Garrett, I et al., (Methods Mol Med, 2003. 80: p. 183-198).

Briefly fifteen newborn, 4 day old Balb/c pubs were used for these experiments. Calvarial bones were dissected under sterile conditions and placed on sterile grids in 12 well plates containing culture media. Calvarial bones were cultured for 10 days in the presence of free γToc, BP-γToc or free BP. Bone morphogenetic protein 2 (BMP-2) was used as a positive control, with known bone anabolic activity in this assay.

Treatments were carried out in quadruplicate as shown below. Calvarial bones were embedded in paraffin wax and sections were stained with haematoxylin and eosin stain (H&E) and analysed using the nanozoom image analysis software.

Treatment groups (4 reps of each):
Untreated
Bpp(OEt) (BP) (15 μM)
BP (20 μM)
γ-Tocotrienol (15 μM)
γ-Tocotrienol (20 μM)
γ-Tocotrienol (100 μM)
BP-γ-tocotrienol conjugate (15 μM)
BP-γTocotrienol conjugate (20 μM)
BP-γ-Tocotrienol conjugate (100 μM)
BMP-2 (50 ng/ml)

Figure 7:
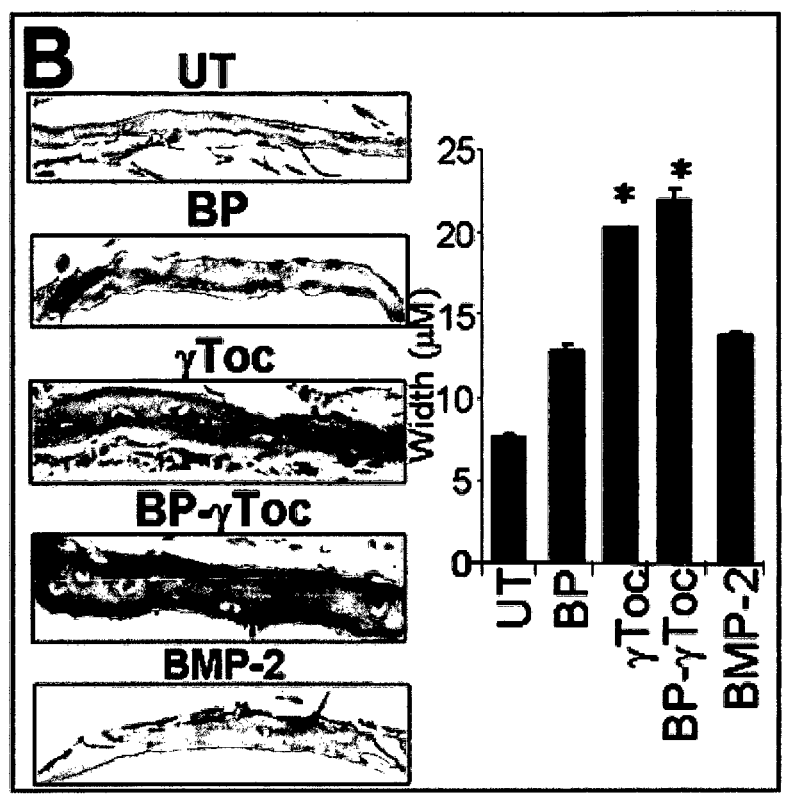
FIG. 7 shows cross sectional photographs after cavarial bones were cultured ex-vivo for 10 days in the presence of drug. The photographs illustrate the extent of bone formation induced by each treatment and the chart provides quantitation of the area of bone growth (n=4/gp, *p<0.001).

New bone formation in treated calvariae was assessed by histological assessment of stained sections. FIG. 7 shows that both free γToc and BP-γToc significantly increased bone formation in calvariae above those treated with free BP or untreated calvariae.

Interestingly, we observed that bone formation induced by BP-γToc conjugate was far superior to the free γToc in this activity. Importantly, this anabolic activity of the conjugated compound was even greater than that seen with the BMP-2 positive control, indicative of a remarkable anabolic action of the conjugated compound (FIG. 7).

Intratibial Injection of Compounds

Four week old female Balb/c Nu/Nu mice were housed under pathogen free conditions, in accordance with the guidelines approved by the Institute of Medical and Veterinary Science animal ethics research committee. Mice were randomly assigned into 3 groups of 4 animals. The left tibia was wiped with 70% ethanol and a 26 gauge needle coupled to a Hamilton syringe, was inserted through the tibial plateau with the knee flexed and 10 μl of each drug injected into the marrow space. Mice were humanely killed 3 weeks post drug administration and bone morphometric parameters were assessed using high resolution micro-CT and histology.

Treatment groups were:
Group 1: Bpp(OEt) (BP) (20 μM)
Group 2: γ-Tocotrienol (20 μM)
Group 3: γ-Tocotrienol-BP conjugate (20 μM)

Micro-Computer Tomography Analysis

Both the right and left tibiae of each animal were mounted in the CT specimen tube and placed securely into the SkyScan-1072 X-ray micro-CT Scanner (Aartselaar, Belgium). The program was commenced with magnification set to give scan slices of 5.2 microns. Three-dimensional (3D) images were generated using Cone-Beam reconstruction and 3D visualisation (Skyscan). Using the two dimensional (2D)

images obtained from the micro-CT scan, the growth plate was identified and 750 sections, starting from the growth plate/tibial interface and moving down the tibia, were selected. Bone volume (mm³) was generated and compared to the control tibia for each animal.

Histology

Tibiae were fixed in 10% buffered formalin, followed by acid decalcification in 10% EDTA solution and 7% nitric acid at room temperature. Decalcification was confirmed by radiography before sectioning. Samples were paraffin embedded, sectioned longitudinally at 6 µM and stained with haemotoxylin and eosin.

Results

Figure 8:
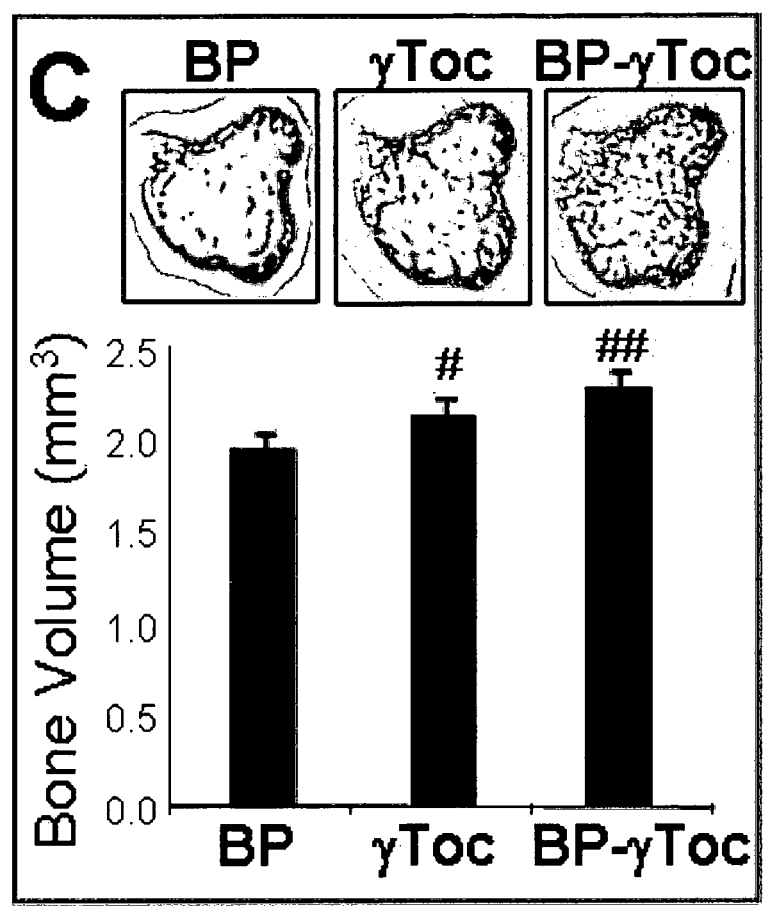
FIG. 8 shows the results by µCT after compounds (15 µM) were injected in the tibial cavity of mice (n=4) and 3 weeks later the trabecular volume was assessed, p<0.01.

Preliminary data show a significant increase in trabecular bone volume at the site of injection, with both the free γToc and BP-γToc conjugate, when compared to the maternal BP compound (FIG. 8).

Mouse Models of Cancer-Induced Bone Destruction
Intratibial Cancer Cell Transplantation In this model, osteolytic breast cancer MDA-MB-231-TXSA cells were transplanted directly into the marrow cavity of tibiae of mice, producing local bone lesions. This model results in localised tumour growth at a single bony site that produces a consistent measurable outcome, in which the efficacy of drug treatment can be accurately assessed.

MDA-MB-231-TXSA breast cancer cells were tagged with a triple reporter gene construct (NES-TGL), and this has been used by us to monitor tumour growth in live animals using fluorescence/bioluminescence imaging.

Cancer cells expressing NES-TGL (1×105 cells/10γl inoculum) were injected into the left tibiae of nude mice (BALB/c, nu/nu), whereas the control (right) tibiae were injected with vehicle. Tumours were allowed to establish to a defined size, as determined by luciferase photon counts (relates directly to tumour burden). Tumour growth is monitored using the Xenogen IVIS 100 imaging system. The extent of osteolysis was assessed using the Skyscan 1076 high resolution ex vivo µ-CT.

A total of 20 four-week old Balb/c nude mice were used for these experiments. The mice were randomly assigned to 4 groups (5 mice/group)

Group 1 is the control mice treated with vehicle (PBS) alone.

Group 2 were injected i.p with the free bpp(OEt) (BP) at (50 mg/kg/dose).

Group 3 were injected i.p with free γ-tocotrienol at (50 mg/kg/dose)

Group 4 were injected i.p with conjugated BP-γTocotrienol conjugate (50 mg/kg/dose).

Treatment was initiated 7 days post cancer cell transplantation for 5 consecutive days followed by two days of rest for two week.

Figure 9:
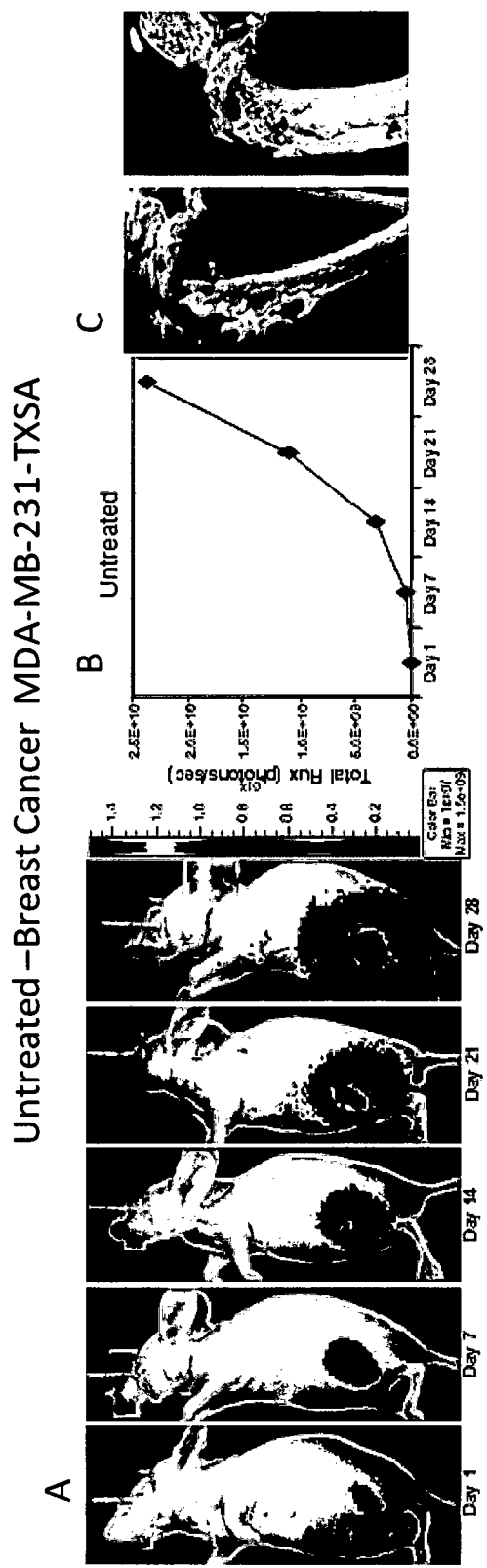
FIG. 9 shows the results of treating mice with compounds disclosed herein after MDA-MB-231-TXSA cells were transplanted directly into the marrow cavity of the tibiae.

Results—Assessment of Tumour Growth and Osteolysis (a) Bioluminescence: A limitation in measuring tumour burden in bone is that it is not possible to assess the progression of tumour growth within the bone because, unlike in the soft tissues, it is not possible to palpate these tumours. However, the bioluminescence whole body live imaging system, gives us an extremely sensitive capability of tracking tumour size in bone and in real time. FIG. 9 shows the untreated group. FIG. 9A shows longitudinal in vivo bioluminescence/fluorescence assay on the same BALB/c, nu/nu mouse injected with MDA-MB-231-TXSA transfectants. The gray scale data correlate with photon counts over time (B), indicating successful growth of the orthotopic tumor. High resolution micro-CT ex vivo reveals highly osteolytic lesions (C).

Figure 10:
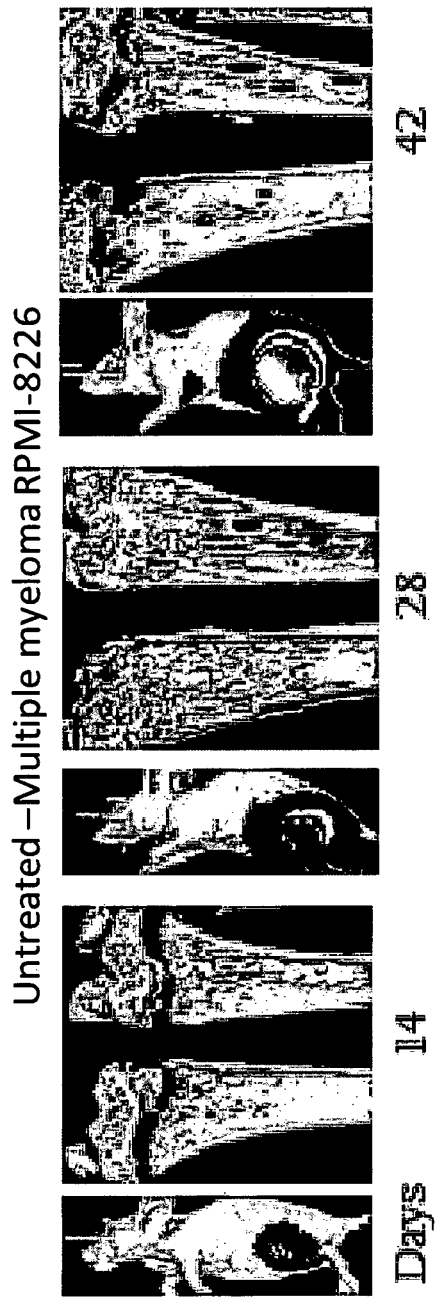
FIG. 10 shows a side by side comparison of in vivo optical imaging and ex vivo micro-CT of the same mouse subjected to orthotopic development of myeloma tumor (combined osteolytic and osteoblastic lesions).

(b) High resolution ex vivo micro-CT analysis: Tibiae from each mouse have been scanned using the high resolution (5 γm sections) in vitroγCT to obtain detailed information of micro-architectural bone parameters. By combining γCT and 3-D reconstruction of each tibia, we are able to follow bone volume and structure longitudinally across cancer development (FIG. 10).

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise paragraphed. No language in the specification should be construed as indicating any non-paragraphed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the paragraphs appended hereto as permitted by applicable law.

The invention claimed is:

1. A compound of formula (I), or a salt or solvate thereof:

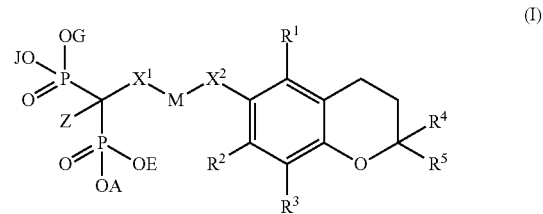

wherein,

A, E, J and G are independently selected from hydrogen and $C_{1-6}$ alkyl;

Z is selected from hydrogen, halogen, hydroxyl, aryl, heteroaryl, and $C_{1-6}$ alkyl, wherein said aryl, heteroaryl and $C_{1-6}$ alkyl may optionally be substituted by one or more $R^z$ groups;

$R^z$ is selected from hydrogen, hydroxyl, halogen, COOH, CN, $C_{1-6}$ haloalkyl, $C_{1-6}$ haloalkoxy, $C_{3-6}$ cycloalkyl, $C_{1-6}$ alkyl and O—$C_{1-6}$ alkyl;

$X^1$ is a $(CR'R'')_n$ group and $X^2$ is a $(CR'R'')_m$ group, wherein R' and R'' are independently selected from hydrogen and $C_{1-6}$ alkyl and m and n are numbers independently selected from 0 to 5;

M is selected from N(R), S, O and C(O)O; wherein R is selected from hydrogen and $C_{1-6}$ alkyl;

$R^1$, $R^2$ and $R^3$ are independently selected from hydrogen and $C_{1-6}$ alkyl;

$R^4$ is a $C_{1-6}$ alkyl group;

$R^5$ is selected from:

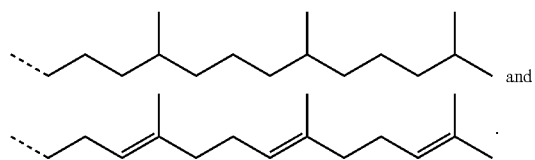

2. The compound of claim 1 wherein A, E, J and G are independently selected from hydrogen, methyl and ethyl.

3. The compound of claim 1 wherein A, E, J and G are all hydrogen or all ethyl.

4. The compound of claim 1 wherein $X^1$ is $(CH_2)_n$ and n is a number selected from 2 and 3.

5. The compound of claim 1 wherein M is O and n is 3.

6. The compound of claim 1 wherein M is C(O)O and n is 2.

7. The compound of claim 1 wherein Z is hydrogen.

8. The compound of claim 1 wherein m is 0.

9. The compound of claim 1 wherein $R^1$, $R^2$, and $R^3$ are independently selected from hydrogen or methyl.

10. The compound of claim 1, wherein $R^1$, $R^2$ and $R^3$ are methyl.

11. The compound of claim 1, wherein $R^1$ is methyl, $R^2$ is hydrogen and $R^3$ is methyl.

12. The compound of claim 1, wherein $R^1$ is hydrogen, $R^2$ is methyl and $R^3$ is methyl.

13. The compound of claim 1, wherein $R^1$ is hydrogen, $R^2$ is hydrogen and $R^3$ is methyl.

14. The compound of claim 1 wherein $R^4$ is methyl.

15. The compound of claim 1 wherein $R^5$ is

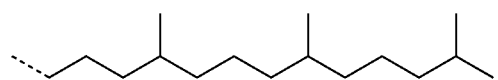

16. The compound of claim 1 wherein $R^5$ is

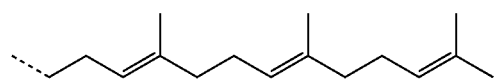

17. The compound of claim 1, wherein the compound is selected from:

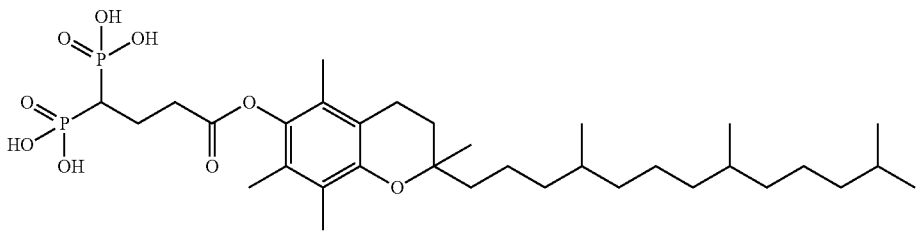

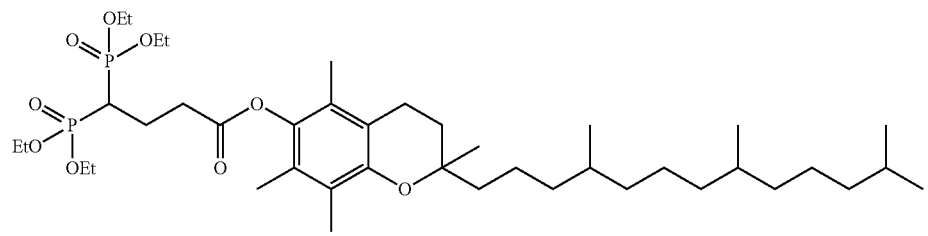

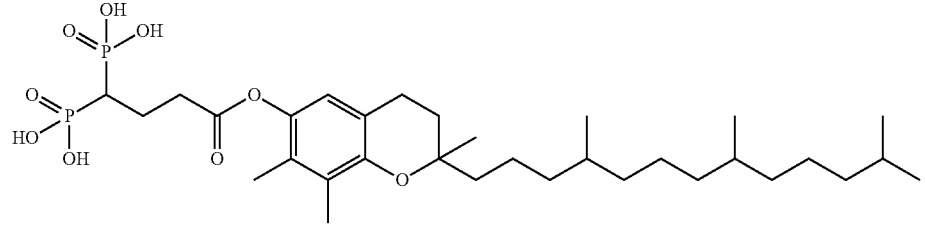

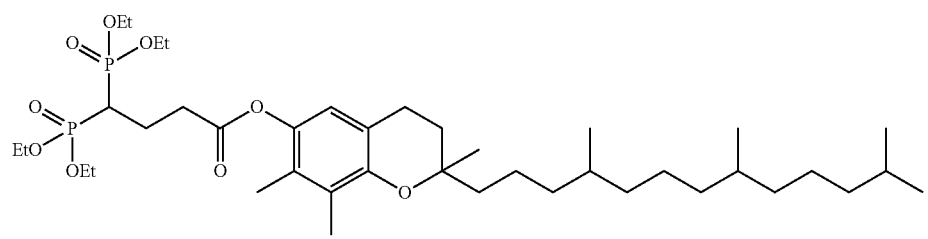

-continued
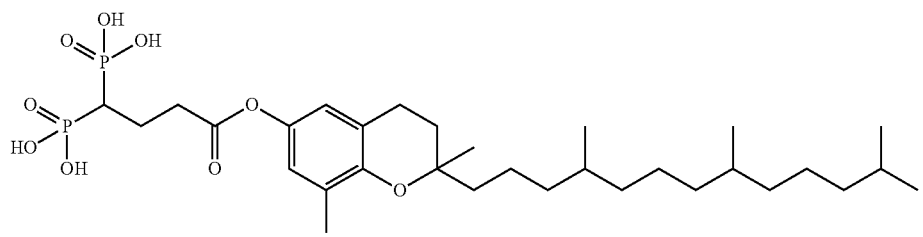
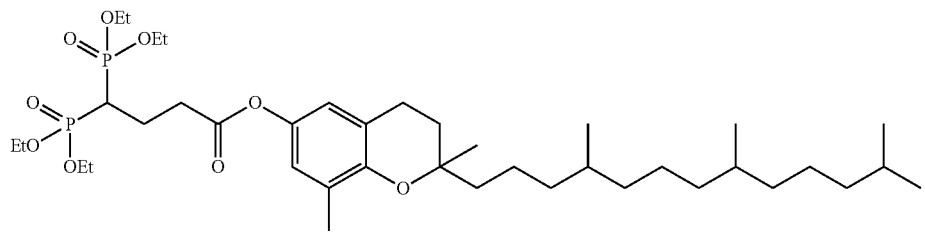
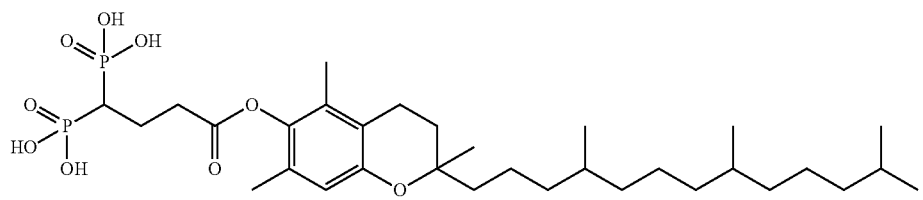
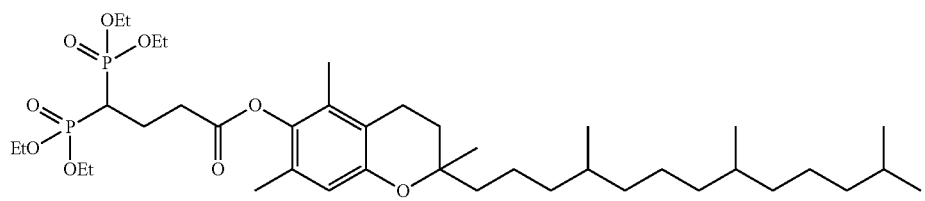
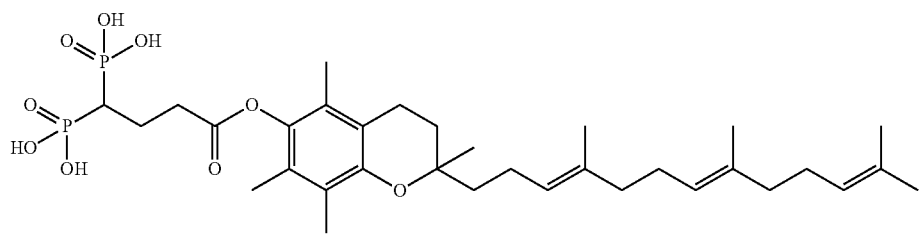
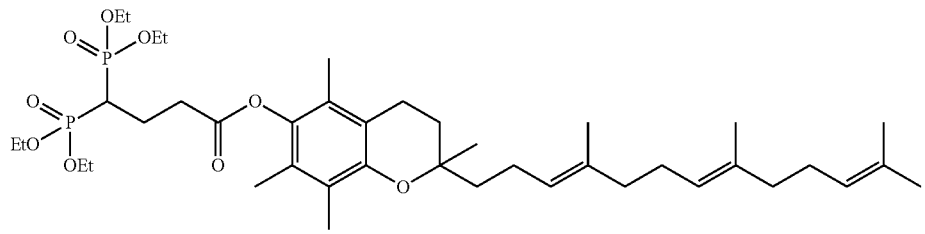
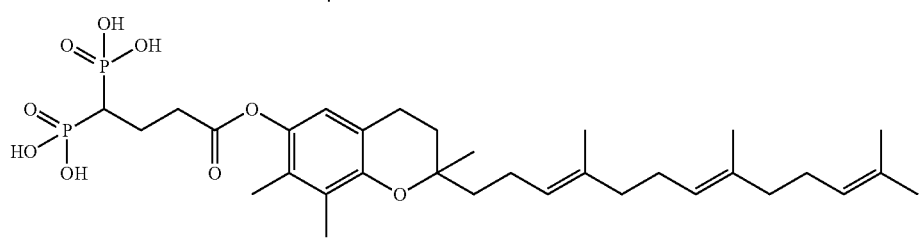

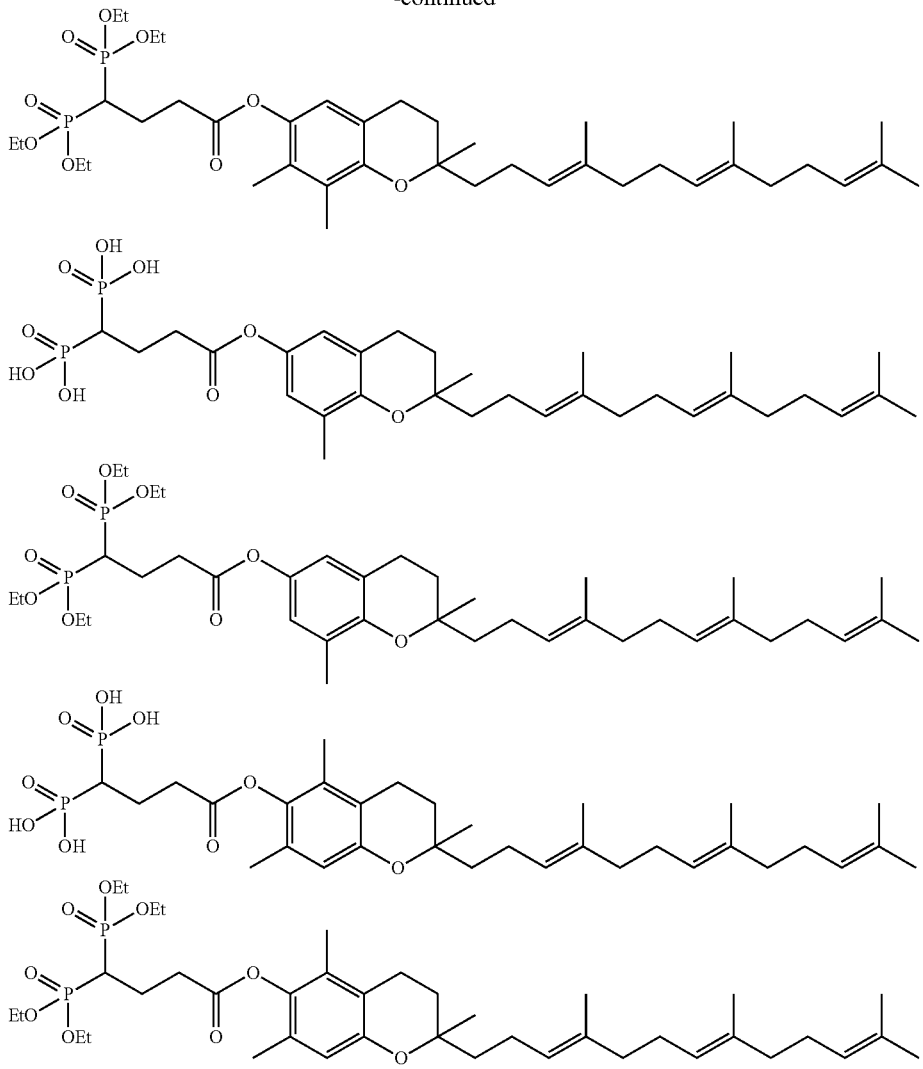

and pharmaceutically acceptable salts or solvates thereof.

18. A pharmaceutical composition comprising the compound of claim 1, or a pharmaceutically acceptable salt or solvate thereof, in admixture with a pharmaceutically acceptable diluent or carrier.

19. A method of treating a proliferative disorder in a patient in need of such treatment, said method comprising administering to said patient a therapeutically effective amount of the compound of claim 1, or a pharmaceutically acceptable salt or solvate thereof.

20. The method of claim 19, wherein the proliferative condition is bone cancer.

21. A combination comprising a compound, or a pharmaceutically acceptable salt or solvate thereof, as defined claim 1, with one or more additional therapeutic agents.

* * * * *